United States Patent
Stamper et al.

(10) Patent No.: US 6,659,972 B2
(45) Date of Patent: Dec. 9, 2003

(54) HALO ORTHOSIS

(75) Inventors: Richard E. Stamper, Terre Haute, IN (US); Matthew P. Meek, Columbus, IN (US)

(73) Assignee: Rose-Hulman Institute of Technology, Terre Haute, IN (US)

(*) Notice: Subject to any disclaimer, the term of this patent is extended or adjusted under 35 U.S.C. 154(b) by 2 days.

(21) Appl. No.: 09/776,526

(22) Filed: Feb. 2, 2001

(65) Prior Publication Data

US 2002/0151831 A1 Oct. 17, 2002

(51) Int. Cl.[7] .................................................. A61F 5/00
(52) U.S. Cl. .......................... 602/17; 602/18; 602/37; 602/40; 606/56; 606/59; 128/846
(58) Field of Search .................... 602/5, 40, 17–19, 602/74, 32–37, 39; 128/846, 857, 874, DIG. 23; 482/10; 606/54, 56, 59, 72–73, 104, 103

(56) References Cited

U.S. PATENT DOCUMENTS

| | | | |
|---|---|---|---|
| 2,706,982 A | | 4/1955 | Hale et al. |
| 3,072,118 A | * | 1/1963 | Standerwick ................ 602/37 |
| 3,099,441 A | | 7/1963 | Ries |
| 3,604,412 A | * | 9/1971 | Gardner ...................... 602/37 |
| 4,444,179 A | * | 4/1984 | Trippi ......................... 602/37 |
| 4,541,421 A | | 9/1985 | Iversen et al. |
| 4,620,530 A | | 11/1986 | Lanier et al. |
| 4,667,660 A | | 5/1987 | Eingorn |
| 4,735,196 A | | 4/1988 | Krag et al. |
| 5,042,462 A | * | 8/1991 | Bremer ........................ 602/37 |
| 5,062,415 A | | 11/1991 | Weatherby et al. |
| 5,109,835 A | * | 5/1992 | McDonald et al. ....... 602/32 X |
| 5,156,588 A | | 10/1992 | Marcune et al. |
| 5,171,296 A | | 12/1992 | Herman |
| 5,203,765 A | | 4/1993 | Friddle, Jr. |
| 5,261,873 A | | 11/1993 | Bremer et al. |
| 5,378,042 A | * | 1/1995 | Daneshvar ................ 602/13 X |
| 5,456,266 A | | 10/1995 | Brown |
| 5,537,704 A | * | 7/1996 | Dinkler ......................... 5/622 |
| 5,624,387 A | * | 4/1997 | McGuinness ................ 602/18 |
| 5,674,186 A | | 10/1997 | Guigui et al. |
| 5,697,895 A | | 12/1997 | Bremer |
| 5,961,528 A | | 10/1999 | Birk et al. |
| 5,984,836 A | * | 11/1999 | Casali ......................... 482/10 |
| 6,179,846 B1 | * | 1/2001 | McFadden .................. 606/130 |

OTHER PUBLICATIONS

Bernardoni CO, Gene, "The Halo Part I," http://www.ballert.com.
Bernardoni CO, Gene, "Part II Application of the Halo to the Patient," http://www.ballert.com.
Bernardoni CO, Gene, "Part III Problems Which May Arise With Halo Fixation," http://www.ballert.com.
Bernardoni CO, Gene, "Part IV A Clinical Review of the Use of the Halo," http://www.ballert.com.
Bernardoni CO, Gene, "Part V Major Available Halo Systems," http://www.ballert.com.
Botte, Michael J. et al., "The Halo Skeletal Fixator (Principles of Application and Maintenance)," *Clinical Orthopaedics and Related Research*, No. 239 Feb. 1989.
Fleming, Braden C., et al., "Pin Loosening in a Halo–Vest Orthosis," SPINE vol. 25, No. 11, pp 1325–1331, published in 2000 by Lippincott Williams & Wilkins, Inc.

(List continued on next page.)

*Primary Examiner*—Nicholas D. Lucchesi
*Assistant Examiner*—Victor Hwang
(74) *Attorney, Agent, or Firm*—Bose McKinney & Evans LLP

(57) ABSTRACT

An apparatus and method are provided for restricting movement of a patient's head. The apparatus includes a frame and a plurality of constraints engaged with the frame to exactly constrain the patient's head relative to the frame.

12 Claims, 13 Drawing Sheets

OTHER PUBLICATIONS

Ballock, R. Tracy, et al., "The Effect of Pin Location on the Rigidity of the Halo Pin–Bone Interface," vol. 26, No. 2, 1990, *BioMechanics of Halo Pin Fixation*, Feb. 1990.

Voor, Micheal J. and Cyna Khalily, "Halo pin loosening: a biomechanical comparsion of experimental and conventional designs," *Journal of Biomechanics*, 1998.

Nickel, V., et al., "The Halo: A Spinal Skeletal Traction Fixation Device," *Clinical Orthopaedics and Related Research*, No. 239, Feb. 1989.

Fleming, Braden C., et al., "Pin force measurement in a holo–vest orthosis, in vivo," *Journal of Biomechanics*, vol. 31, 1998, 647–651.

S. Liu, et al., "The Effect of Local Halo Pin Care Reagents on Cranial Radia Compressive Stress (When Tightening Halo Pins)," *Journal of Prosthetics and Orthostics*, vol. 5, No. 3, 67–72, 1993.

Botte, M., et al., "Application of the Halo Device for Immobilization of the Cervical Spine Utilizing an Increased Torgue Pressure," *The Journal of Bone anf Joint Surgery*, vol. 69, No. 5, 1987.

Letts, M., et al., "Mechanical Evaluation of Four–Versus Eight–Pin Halo Fixation," *Journal of Pediatric Orthopaedics*, vol. 17, 121–124, 1997.

Garfin, S.,et al., "Structural Behavior of the Halo Orthosis Pin–Bone Interface: Biomechanical Evaluation of Standard and Newly Designed Stainless Steel Halo Fixation Pins," *Spine*, vol. 11, No. 10, 1986.

Vertullo, Christopher J., et al., "Pin–Site Complications of the Halo Thoracic Brace With Routtine Pin Re–Tightening," *Spine*, vol. 22, No. 21, pp. 2514–2516.

Tsai, L. and Stamper, R., "A Parallel Manipulator with Only Translational Degrees of Freedom" *Proceedings of the 1996 ASME Design Engineering Technical and Computers in Engineering Conference*, MECH: 1152, 1996.

Bullock, Stacy J. and Runciman, R. John, "Biomechanical evaluation of two halo pin design, with, and without, intact periosteum", *Journal of Biomechanics*, 2001, pp. 129–133.

Triggs, Kevin J., MD, et al., "The Effect of Angled Insertion on Halo Pin Fixation,"*Division of Orthopaedics and Rehabilitation, University of California*, 1998.

Norton, Robert L., *Design of Machinery*, $2^{nd}$ Edition, McGraw–Hill, copyright 1999, ISBN: 0–07–048395–7, pp. 28–32.

Tsai, Lung–Wen, *Mechanism Design: Enumeration of Kinematic Structures According to Function*, CRC Press, copyright 2000, ISBN: 0–8493–0901–8, pp. 66–70.

PMT Corp., Halo Systems, PMT Model 1233, http://www.pmtcorp.com/halo.htm.

Tsai, Lung–Wen, *Robert Analysis—The Mechanics of Serial and Parallel Manipulators*, John Wiley and Sons (1999), pp. 9–15.

Norton, Robert L. *Design of Machinery—An Introduction To The Synthesis and Analysis of Mechanisms and Machines*, McGraw–Hill (1999).

* cited by examiner

HALO ORTHOSIS

FIELD OF THE INVENTION

This invention relates to halo orthoses, and, more particularly, to an apparatus and method for exactly constraining patients' heads within halo orthoses.

BACKGROUND

A halo orthosis minimizes motion of the cervical spine after traumatic injury or in recovery after surgery. To immobilize the cervical spine, the halo orthosis provides a rigid structure that fixes the head of the patient relative to the patient's chest. The standard halo orthosis includes a crown or halo ring and halo pins that secure the halo ring to the head of the patient. The basic design of the halo orthosis has changed very little since its introduction in 1959.

Two of the most common problems associated with halo orthoses are pin loosening and/or pin migration (hereinafter referred to jointly and severally as "pin loosening"). To ensure that the head is properly fixed, the halo pins typically must pierce through the skin and rest against or embed in the skull. However, bone remodeling at the pin sites, changes in the elasticity of the head or skull, and/or other physiological changes in the head or skull geometry typically cause the pins to loosen over time. Proactive and/or corrective pin adjustments require undesirably complex and costly follow-up care by highly skilled medical professionals (typically orthopedic surgeons). For the patient, pin loosening can cause significant pain, potential loss of immobilization, and an increased risk of infection.

Indeed, infection is another common problem with halo orthoses. As the halo pins typically pierce the skin, each pin site creates a wound that is vulnerable to infection. Notwithstanding any loosening and/or retightening of the pins, the undesirably high number of pin sites in prior designs adds to the risk of infection.

The application procedures for prior halo orthoses also present problems. Historically, an orthopedic surgeon or team of orthopedic surgeons has been required to manually balance the torque among the various separate pins in order to properly apply the halo. Typically, such procedures are painful to the patient and require significant amounts of time and skill from the orthopedic surgeons.

Thus, there is a need for a halo orthosis that provides reduced pin loosening. Also, there is a need for a halo orthosis that requires a minimal number of pin sites. Additionally, there is a need for a halo orthosis that requires less time and skill to apply.

SUMMARY OF THE INVENTION

The present invention provides an apparatus for restricting movement of a patient's head. The apparatus includes a frame and a plurality of constraints engaged with the frame to exactly constrain the patient's head relative to the frame.

In one embodiment, the plurality of constraints includes a first constraint engaged with the frame to permit exactly three degrees of motion of the patient's head relative to the frame, a second constraint engaged with the frame to permit exactly four degrees of motion of the patient's head relative to the frame, and a third constraint engaged with the frame to permit exactly five degrees of motion of the patient's head relative to the frame.

In an alternative embodiment, the plurality of constraints includes a first constraint engaged with the frame to permit exactly four degrees of motion of the patient's head relative to the frame, a second constraint engaged with the frame to permit exactly four degrees of motion of the patient's head relative to the frame, and a third constraint engaged with the frame to permit exactly four degrees of motion of the patient's head relative to the frame.

In another alternative embodiment, the plurality of constraints includes a first constraint engaged with the frame to permit exactly five degrees of motion of the patient's head relative to the frame, a second constraint engaged with the frame to permit exactly five degrees of motion of the patient's head relative to the frame, a third constraint engaged with the frame to permit exactly four degrees of motion of the patient's head relative to the frame, and a fourth constraint engaged with the frame to permit exactly four degrees of motion of the patient's head relative to the frame.

In another alternative embodiment, the plurality of constraints includes a first constraint engaged with the frame to permit exactly five degrees of motion of the patient's head relative to the frame, a second constraint engaged with the frame to permit exactly five degrees of motion of the patient's head relative to the frame, a third constraint engaged with the frame to permit exactly five degrees of motion of the patient's head relative to the frame, and a fourth constraint engaged with the frame to permit exactly three degrees of motion of the patient's head relative to the frame.

In another alternative embodiment, the plurality of constraints includes a first constraint engaged with the frame to permit exactly five degrees of motion of the patient's head relative to the frame, a second constraint engaged with the frame to permit exactly five degrees of motion of the patient's head relative to the frame, a third constraint engaged with the frame to permit exactly five degrees of motion of the patient's head relative to the frame, a fourth constraint engaged with the frame to permit exactly five degrees of motion of the patient's head relative to the frame, and a fifth constraint engaged with the frame to permit exactly four degrees of motion of the patient's head relative to the frame.

In another alternative embodiment, the plurality of constraints includes a first constraint engaged with the frame to permit exactly five degrees of motion of the patient's head relative to the frame, a second constraint engaged with the frame to permit exactly five degrees of motion of the patient's head relative to the frame, a third constraint engaged with the frame to permit exactly five degrees of motion of the patient's head relative to the frame, a fourth constraint engaged with the frame to permit exactly five degrees of motion of the patient's head relative to the frame, a fifth constraint engaged with the frame to permit exactly five degrees of motion of the patient's head relative to the frame, and a sixth constraint engaged with the frame to permit exactly five degrees of motion of the patient's head relative to the frame.

In yet another alternative embodiment, the present invention provides a method for restricting movement of a head of a patient with a frame and a plurality of constraints. The method includes the step of exactly constraining the head relative to the frame.

The features and advantages of the present invention described above, as well as additional features and advantages, will be readily apparent to those skilled in the art upon reference to the following detailed description and the accompanying drawings.

DETAILED DESCRIPTION OF EXEMPLARY EMBODIMENTS

Figure 1:
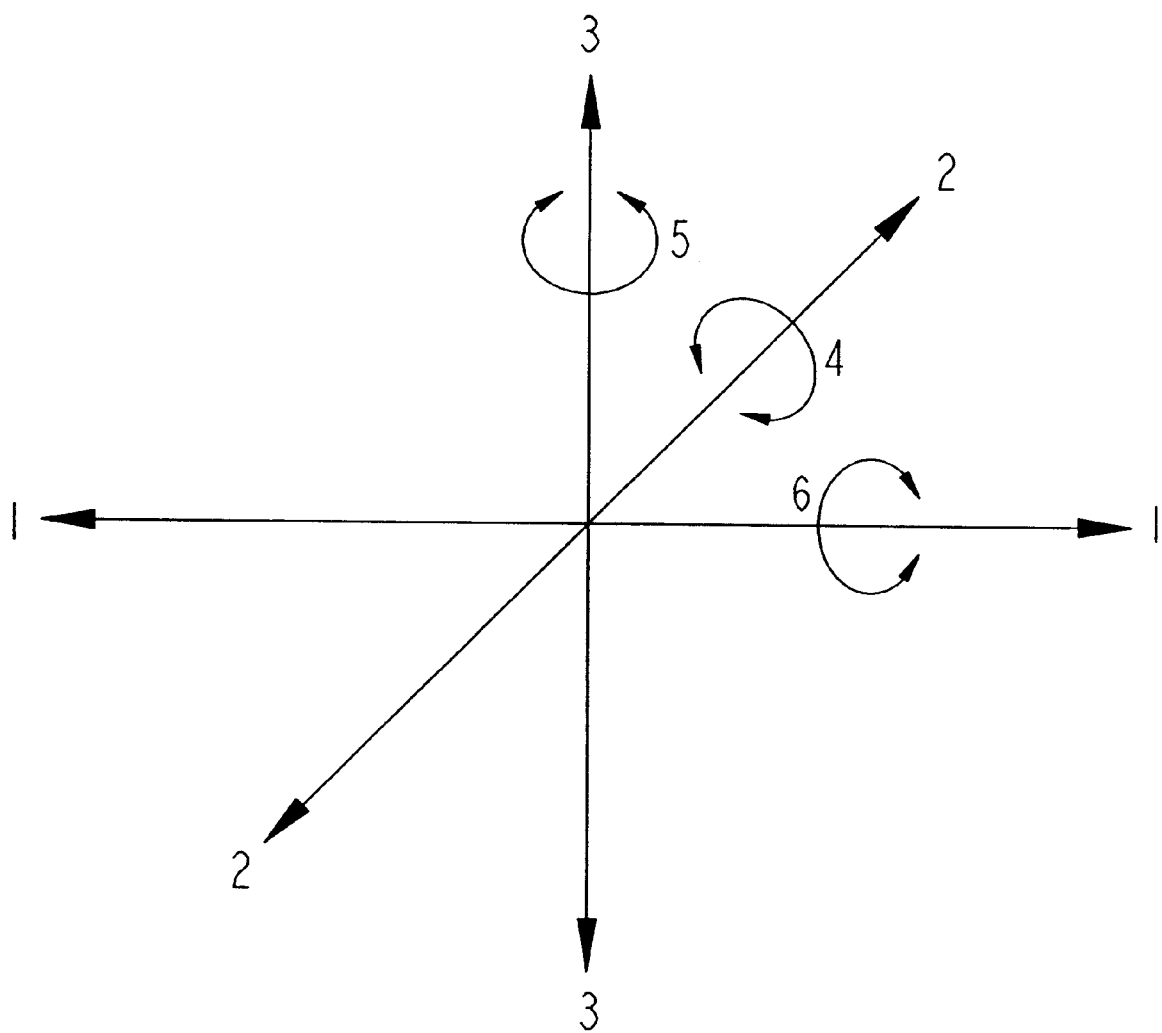
FIG. 1 is a diagram showing 6 spatial degrees of freedom.

In referring to the figures, like parts are identified by like reference numerals throughout.

FIG. 1 is an illustration of the 6 spatial degrees of freedom associated with the movement of a person's head relative to the person's body. As shown in FIG. 1, an object in space has six degrees of freedom: three linear degrees of freedom (one along an x-axis 1, one along a y-axis 2, and one along a z-axis 3), and three rotational degrees of freedom (pitch 4, yaw 5, and roll 6). Mechanisms are often used to constrain one or more of these degrees of freedom. With constraint analysis, the constraint system produced by a mechanism can be categorized as under-constrained, exactly constrained, or over-constrained. In an under-constrained system the mechanism has some mobility. In an over-constrained system one or more constraints remove more degrees of freedom than necessary (i.e., there are redundant constraints). In an exactly-constrained system, however, the constrained item is held without redundant constraints.

Generally, in the context of designing mechanisms and structures, it is undesirable to have an over-constrained system. Over-constrained systems are sensitive to small changes in part geometry such as thermal expansion, and the forces and torques acting within an over-constrained system are difficult to predict.

The Grubler/Kutzbach criteria may be used to determine the category of the constraint system for a given mechanism as follows:

$$F = \lambda(n - j - 1) + \sum_{i=1}^{j} f_i \quad (1)$$

where:

F: degrees of freedom of the mechanism, $\lambda$: The motion parameter defines the degrees of freedom of the space in which a mechanism is intended to function ($\lambda=6$ for spatial mechanisms and $\lambda=3$ for planar mechanisms), n: number of links in the mechanism including the fixed link, j: number of joints in the mechanism, assuming all joints are binary, and $f_i$: degrees of relative motion permitted by the $i^{th}$ joint.

For a fixed mechanism (i.e., a mechanism for which zero degrees of freedom are desired): if F>0 then the mechanism is under-constrained, if F=0 then the mechanism is exactly constrained, and if F<0 then the mechanism is over-constrained.

Figure 2:
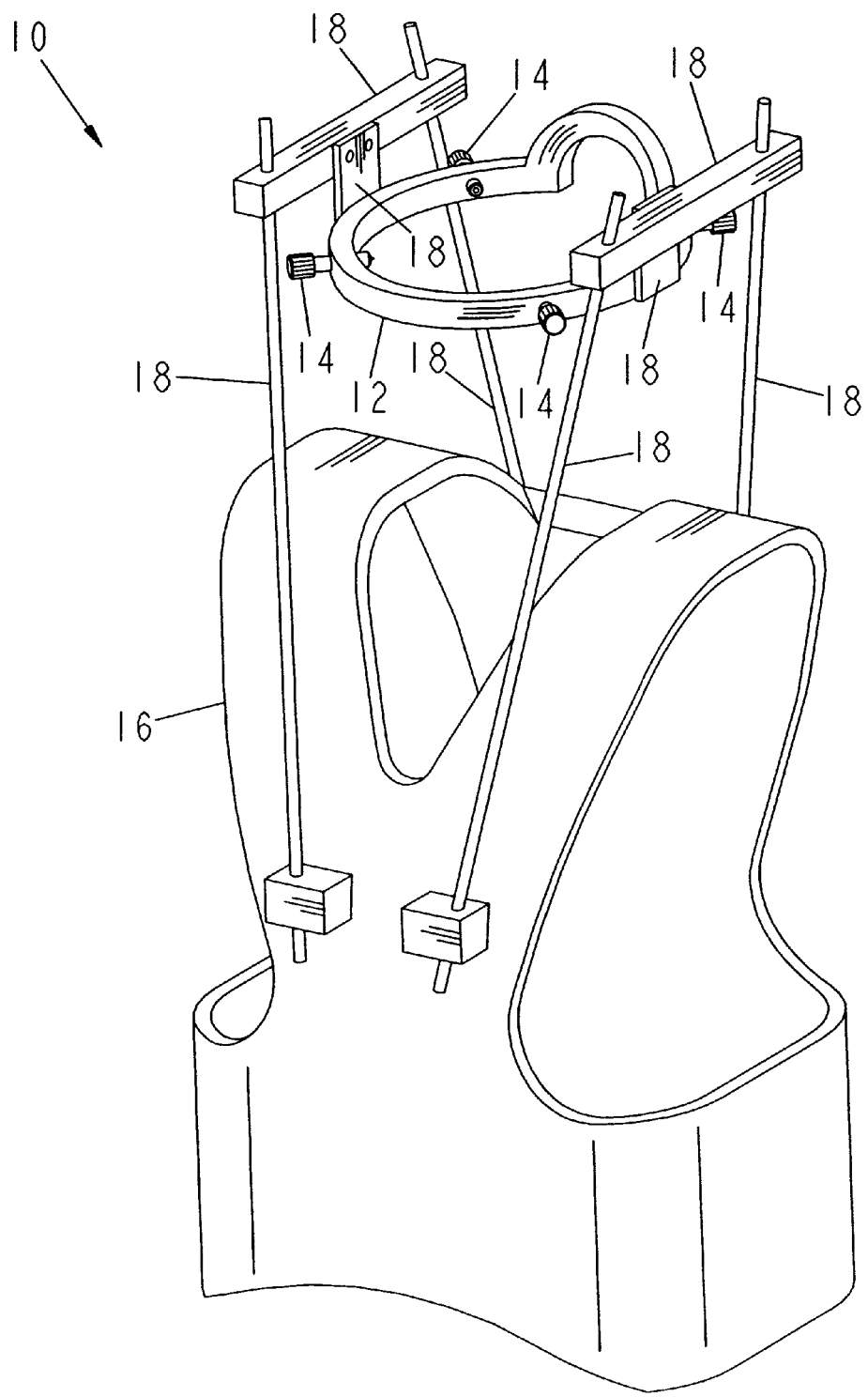
FIG. 2 is a perspective view of a prior art halo orthosis.

FIG. 2 shows a typical prior art halo orthosis 10. The typical prior art halo orthosis 10 includes a crown or halo ring 12, halo pins 14 that secure the halo ring 12 to the head of the patient, a vest 16 that wraps around the patient's chest, and a rod system 18 that connects the vest 16 to the halo ring 12. The typical prior art halo orthosis 10 includes four halo pins 14, each restricting three degrees of linear motion of the patient's head relative to the halo ring 12.

Applying the Grubler/Kutzbach criteria to determine the category of the constraint system in the typical prior art halo orthosis 10 requires that the head and the halo ring/pin assembly be modeled as a mechanism. To this end, the mechanism used to model the halo/head system has two links: the head and the halo ring/pin assembly, so that n=2. Further, each pin/head interface is modeled as a single joint. Since there are four pin/head interfaces, j=4. Each of these pin/head joints acts like a spherical joint since taken individually they constrain linear motion at the joint but permit all three rotational degrees of freedom, hence $f_i=3$ for each of the joints. The motion parameter is six, $\lambda=6$, since the halo is a spatial system. Accordingly, applying the Grubler/Kutzbach criteria to the halo orthosis 10 shown in FIG. 2 produces:

$$F = \lambda(n - j - 1) + \sum_{i=1}^{j} f_i$$

$F=6(2-4-1)+3+3+3+3$ $F=-18+12$ $F=-6$

Thus, the skull is over-constrained relative to the halo ring 12. By reducing the number of halo pins 14 to three (F=−3) the mechanism is still over-constrained. Consequently, the pin forces in the typical prior art halo orthosis 10 (having three or four halo pins) are undesirably difficult to balance during application of the halo pins 14 to the head of the patient. Further, the pin forces are undesirably sensitive to small physiological changes in the geometry of the head or skull that typically occur after application, which exacerbates the pin loosening problem.

Figure 3:
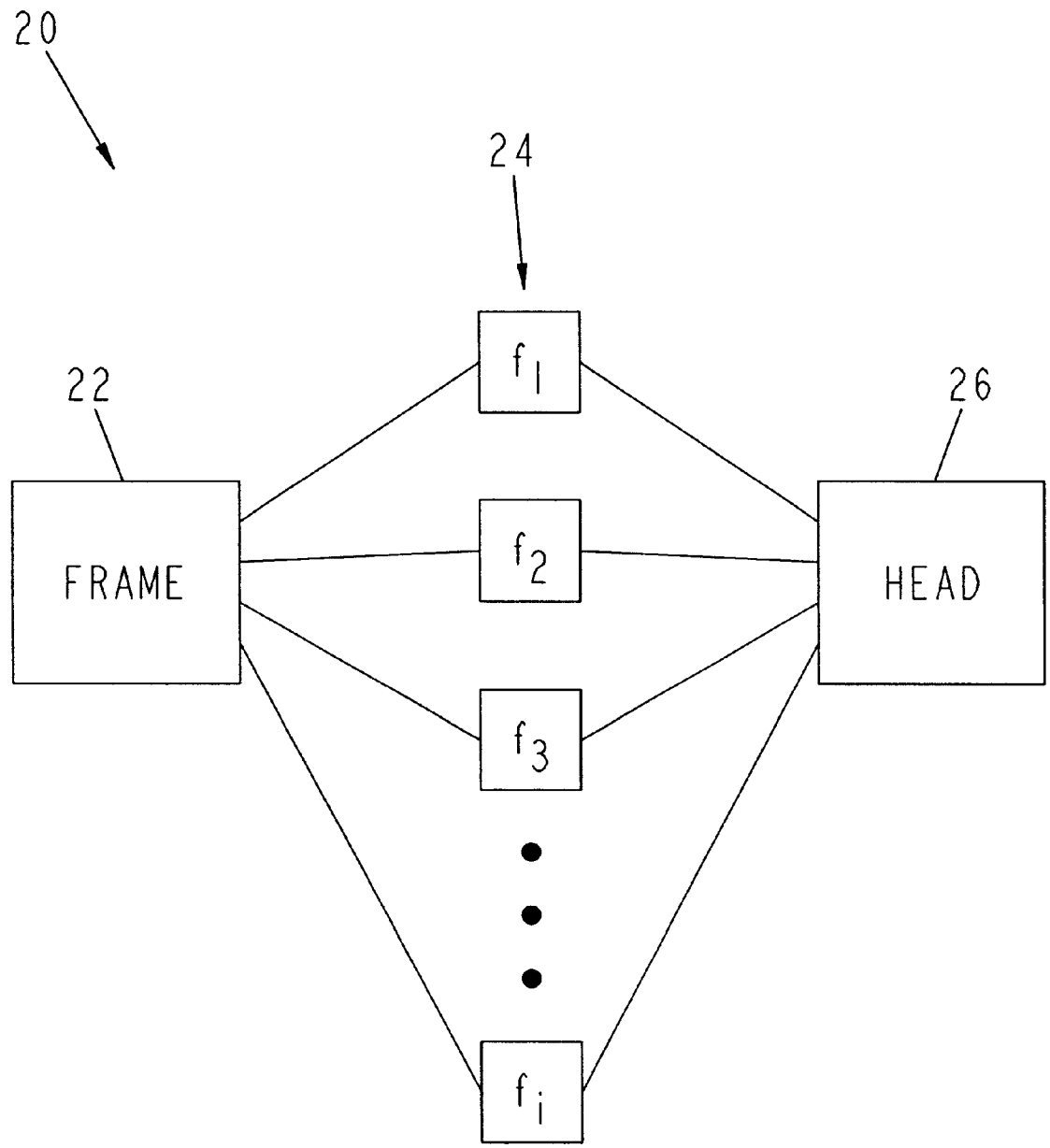
FIG. 3 is a diagrammatic model of an apparatus for restricting movement of a patient's head relative to a frame including a constraint system constructed according to the present invention.

FIG. 3 is a diagrammatic model of an apparatus 20 for restricting movement of a patient's head 26 relative to a frame 22 including a constraint system 24 constructed according to the present invention. The mechanism 20 includes a frame 22, the constraint system 24, and a patient's head 26. In general, the frame 22 is configured to support the constraint system 24 and the constraint system 24 is configured to constrain the head 26 relative to the frame 22. The constraint system 24 includes a plurality of constraints which, in general, each permit $f_i$ degrees of relative motion of the head 26 relative to the frame 22 when considered individually. As used throughout this disclosure and the claims in connection with a halo orthosis constructed according to the present invention, the term "exactly constrained" means that the halo orthosis includes a constraint system having any combination of apparatus providing a result F=0 when the Grubler/Kutzbach criteria are applied to the constraint system.

Accordingly, various alternative embodiments of the present invention exactly constrain the head 26 relative to the frame 22. Some alternative embodiments have only three constraints and others have a number of constraints other than three. TABLE 1 shows some alternative embodiments of the present invention, where the frame 22 (see FIG. 3) is modeled as one link, the head 26 (see FIG. 3) is modeled as one link, each constraint as a whole (see $f_1$, $f_2$, $f_3$, . . . $f_i$ of the constraint system 24 of FIG. 3) is modeled as one joint, the $f_i$ values for each constraint model the degrees of relative motion of the head 26 relative to the frame 22 permitted by the $i^{th}$ constraint as a whole, and "N/A" indicates that the embodiment does not have an $i^{th}$ constraint. It will be appreciated that the specific embodiments of constraint members described herein which provide three, four, and five degrees of freedom of relative motion of the head 26 to the frame 22 can be used in any of the embodiments illustrated by TABLE 1.

TABLE 1

| Table Row No. | F | λ | n | j | λ(n-j-1) | $f_1$ | $f_2$ | $f_3$ | $f_4$ | $f_5$ | $f_6$ |
|---|---|---|---|---|---|---|---|---|---|---|---|
| 1 | 0 | 6 | 2 | 3 | −12 | 3 | 4 | 5 | N/A | N/A | N/A |
| 2 | 0 | 6 | 2 | 3 | −12 | 4 | 4 | 4 | N/A | N/A | N/A |
| 3 | 0 | 6 | 2 | 4 | −18 | 5 | 5 | 4 | 4 | N/A | N/A |
| 4 | 0 | 6 | 2 | 4 | −18 | 5 | 5 | 5 | 3 | N/A | N/A |
| 5 | 0 | 6 | 2 | 5 | −24 | 5 | 5 | 5 | 5 | 4 | N/A |
| 6 | 0 | 6 | 2 | 6 | −30 | 5 | 5 | 5 | 5 | 5 | 5 |

It should be readily appreciated that Row No. 1 of TABLE 1 shows a three constraint embodiment wherein one constraint permits three degrees of relative motion of the head 26 relative to the frame 22, another constraint permits four degrees of relative motion of the head 26 relative to the frame 22, and yet another constraint permits five degrees of relative motion of the head 26 relative to the frame 22. Further, it should be readily appreciated that Row No. 2 shows an alternative three constraint embodiment wherein each of the constraints permits four degrees of relative motion of the head 26 relative to the frame 22. Similarly, Row No. 3 shows an alternative four constraint embodiment wherein two constraints each permit five degrees of relative motion of the head 26 relative to the frame 22 and the other two constraints each permit four degrees of relative motion of the head 26 relative to the frame 22. Row No. 4 similarly shows an alternative four constraint embodiment; Row No. 5 shows an alternative five constraint embodiment; and Row No. 6 rows shows an alternative six constraint embodiment. Further, it should be readily appreciated that other combinations of constraints that exactly constrain the head 26 relative to the frame 22 (for example, those including a constraint having an $f_i=2$, a constraint having an $f_i=1$, or a constraint having an $f_i=0$) are possible and are considered to be within the scope of the present invention. Also, it is noted that in FIG. 3 and TABLE 1 the constraints as a whole are modeled as consolidated joints merely for clarity of exposition. It should be readily appreciated that each constraint of the constraint system 24 may include various suitable alternative arrangements of particular links and joints of its own which, as a whole, effectively yield an appropriate $f_i$ value according to the present invention.

Figure 4:
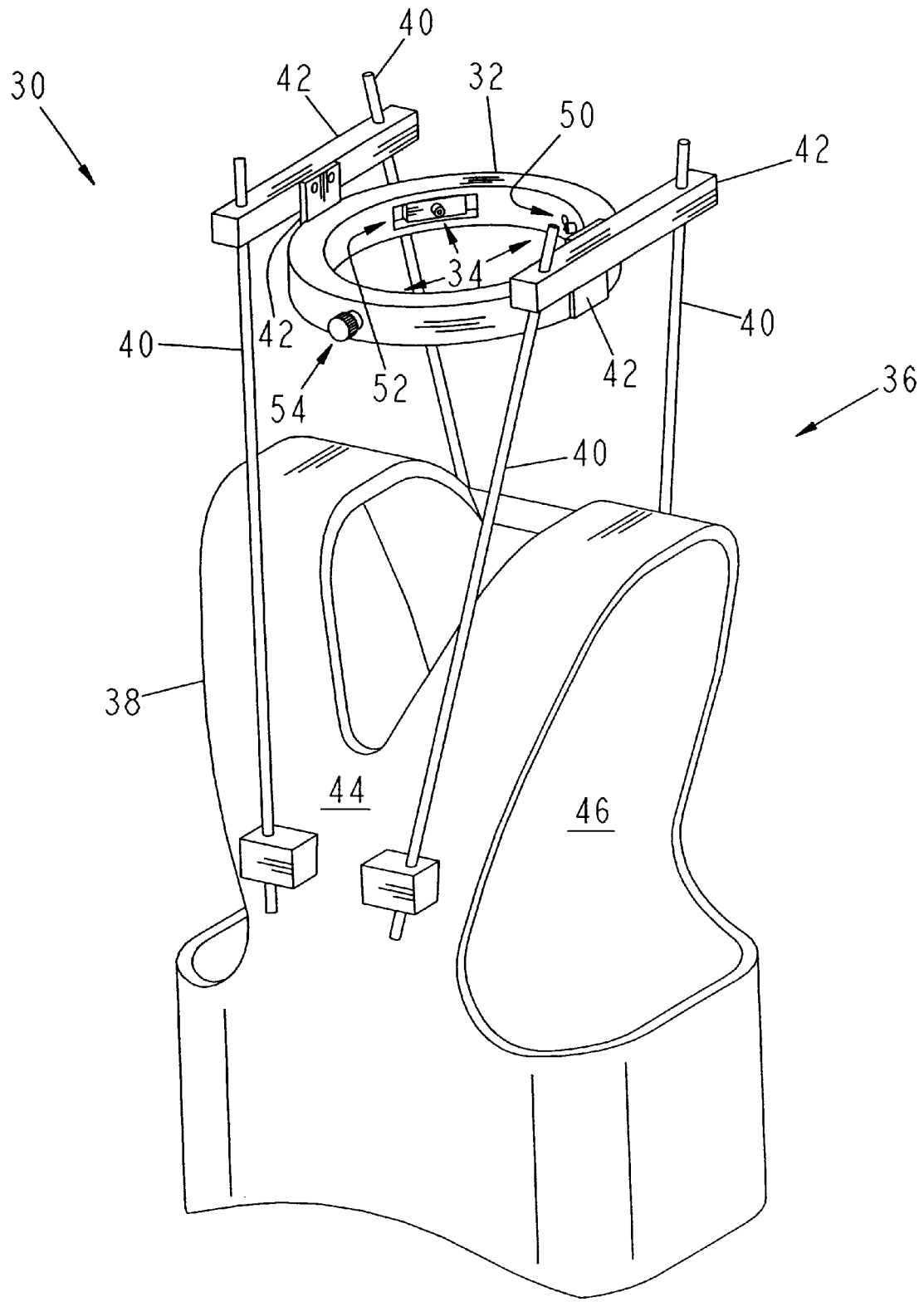
FIG. 4 is a perspective view of one embodiment of a halo orthosis constructed according to the present invention.

FIG. 4 is a perspective view of one embodiment of a halo orthosis 30 constructed according to the present invention. In general, the halo orthosis 30 includes a frame 32, a constraint system 34, and a support structure 36. The support structure 36 includes a vest 38 that is configured to be worn by a patient, and rods 40 and brackets 42 between the vest 38 and the frame 32 that support the frame 32. The vest 38 includes a front portion 44 and rear portion 46 that generally opposes the front portion 44. The front portion 44 is configured to generally extend over the patient's chest and the rear portion 46 is configured to generally extend over the patient's back. Various suitable ways of making and using the support structure 36 and alternative embodiments for the support structure 36 are well known.

In general, the frame 32 and the constraint system 34 are configured to engage the patient's head and to exactly constrain the head relative to the frame 32. The frame 32 and the constraint system 34 are suitably made from an aluminum alloy, titanium, a plastic(s), a combination thereof or other material(s) that are suitably strong yet transparent to magnetic resonance imaging ("MRI"). To this end, various suitable alternative materials are well known. Moreover, MRI transparency is not a limitation of the present invention and, thus, in alternative embodiments the frame 32 and the constraint system 34 may be made from other metal(s) or any other suitable materials. The exemplary constraint system 34 includes a constraint 50, a constraint 52, and a constraint 54. Further details regarding the exemplary frame 32 and the exemplary constraint system 34 are discussed below.

Figure 5:
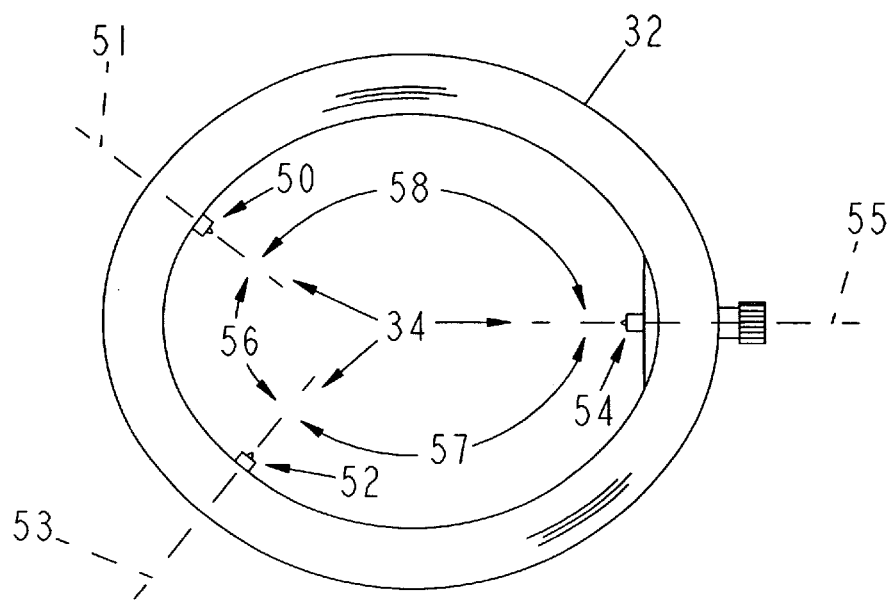
FIG. 5 is a top plan view of a frame and constraint system constructed according to the present invention.

FIG. 5 shows the frame 32 and constraint system 34 constructed according to the present invention. As shown in FIG. 5, the frame 32 is generally oval-shaped. However, in alternative embodiments the frame 32 may be generally C-shaped (see, e.g., FIGS. 10–15), or the frame 32 may be any other shape or configuration that provides a suitable interface between alternative embodiments of the support structure 36 (see FIG. 4) and the constraint system 34. As discussed above, the constraint system 34 includes the constraint 50, the constraint 52, and the constraint 54. The constraint 50 has an axis 51, the constraint 52 has an axis 53, and the constraint 54 has an axis 55. The axis 51 is angularly displaced from the axis 53 by an angle 56, the axis 53 is angularly displaced from the axis 55 by angle 57, and the axis 55 is angularly displaced from the axis 51 by an angle 58. The constraint 50, the constraint 52, and the constraint 54 may be alternatively positioned about the frame 32 according to a number of suitable alternative embodiments, as long as the angle 57 (between the constraint 52, which permits four degrees of relative motion, and the constraint 54, which permits five degrees of relative motion, discussed below) is not a multiple of 90 degrees (i.e., not 90 degrees, not 180 degrees, not 270 degrees, etc.). Further, as shown in FIGS. 4–9, the angle 56, the angle 57, and the angle 58 preferably are each 120 degrees. However, these angles need not be equal in alternative embodiments.

Figure 6:
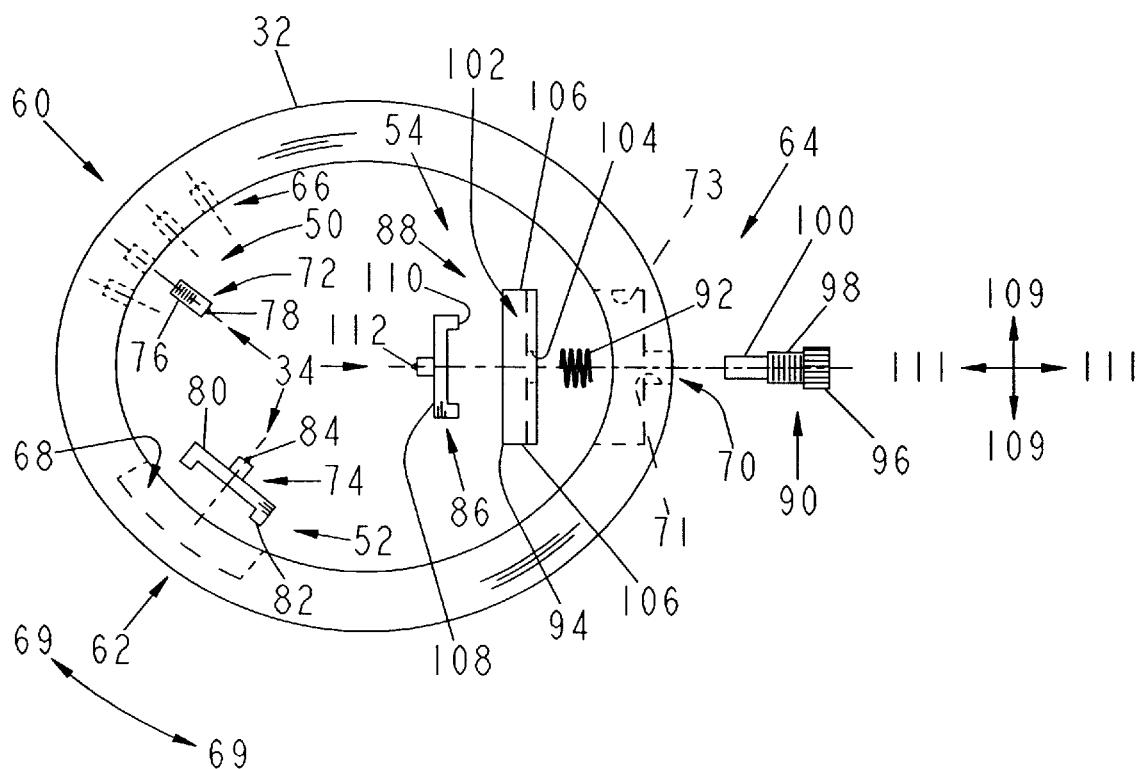
FIG. 6 is an exploded top plan view of the frame and constraint system of FIG. 5.

As shown in FIG. 6, the frame 32 includes a portion 60, a portion 62, and a portion 64. It should be readily appreciated that in the generally oval-shaped frame 32, the portion 60, the portion 62, and the portion 64 are all generally arcuately shaped. The portion 60 of the frame 32 defines a set of apertures 66. It should be readily appreciated that although four apertures are shown, the set of apertures 66 may suitably include a number of apertures other than four. In any event, each of the apertures 66 includes suitable screw threads (not shown). The portion 62 of the frame 32 defines a slot 68 extending arcuately in the inner surface of the frame 32. Although in the embodiment shown in FIG. 6 the slot 68 is arcuate, in alternative embodiments the slot 68 is suitably flat or otherwise shaped such that it permits freedom of movement of a head constraint member 74 as further discussed below. The portion 64 of the frame 32 defines an opening 70 including a reduced portion 71 opening axially outward and an enlarged portion 73 larger than portion 71 opening axially inward. The opening 70 includes suitable screw threads in the reduced portion 71 (not shown).

As shown in FIG. 6, the constraint 50 (see FIGS. 4 and 5) includes a head constraint member 72 and the constraint 52 (see FIGS. 4 and 5) includes the head constraint member 74. The head constraint member 72 includes a threaded portion 76 that is screwed into any desired one of the apertures 66 and fixed within that aperture during operation as discussed further below. The head constraint member 72 further includes a generally pointed head 78 that is configured to pierce the patient's skin and embed in the patient's skull during operation of the exemplary halo orthosis 30 of FIG. 4.

The head constraint member 74 includes an elongated portion 80 that is slidably engaged with the slot 68. It should be readily appreciated that this slidable engagement permits freedom of movement of the head constraint member 74 within the slot 68 along an axis generally parallel to the directional arrows 69. The elongated portion 80 includes bearings 82 at opposing ends that facilitate its slidable engagement with the slot 68. The bearings 82 shown are protruding portions of the elongated portion 80 that act as friction bearings. In alternative embodiments the bearings 82 may be roller bearings, ball bearings, or any other suitable type of bearing. Moreover, it should be readily appreciated that alternative embodiments may suitably omit the distinct bearings 82. The head constraint member 74 further includes a generally pointed head 84 that is configured to pierce the patient's skin and embed in the patient's skull during operation of the exemplary halo orthosis 30 of FIG. 4.

Figure 7:
FIG. 7 is an assembled side view of the frame and constraint system of FIG. 6.
Figure 8:
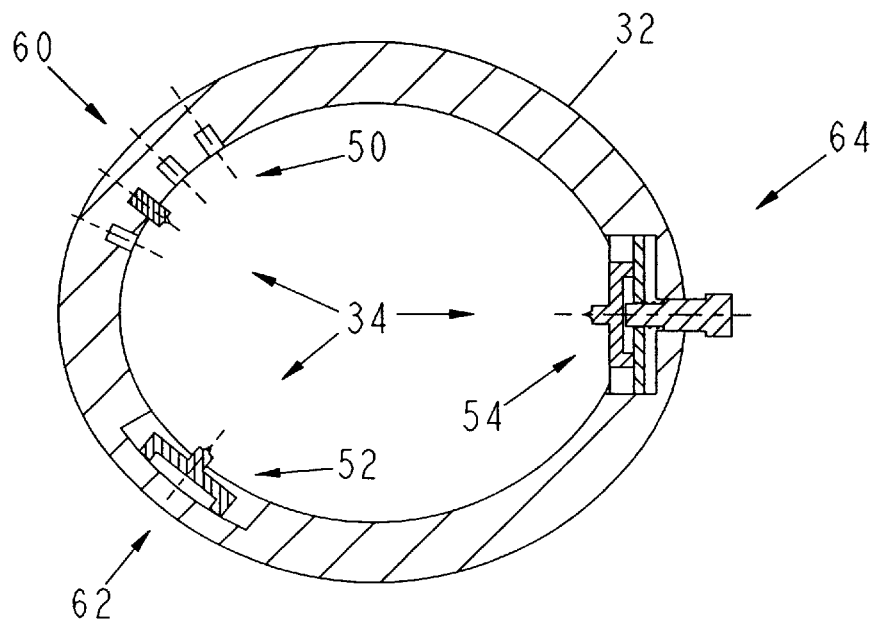
FIG. 8 is an assembled cross-sectional view of the frame and constraint system shown in FIG. 6 taken along line 8—8 of FIG. 7.

As further shown in FIG. 6, the constraint 54 (see FIGS. 4 and 5) includes a head constraint member 86 and a force generator 88. The force generator 88 includes an adjustment member 90, a resilient member 92, and a base member 94 for receiving the head constraint member 86. FIG. 7 shows an assembled side view of the frame 32 and constraint system 34 of FIG. 6, and FIG. 8 shows an assembled cross-sectional view of the frame 32 and constraint system 34 of FIG. 6 along line 8—8 of FIG. 7. Meanwhile, FIG. 9 is an enlarged assembled cross-sectional view of the portion 64 of the frame 32 and constraint 54 shown in FIG. 8, taken along line 8—8 of FIG. 7.

Figure 9:
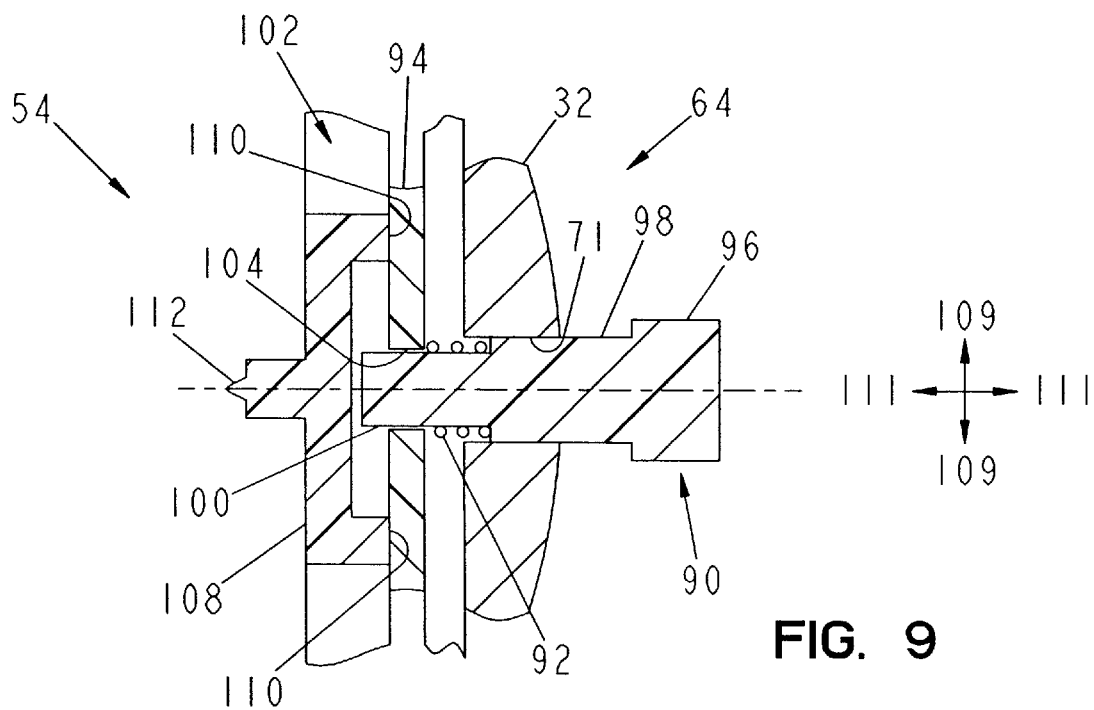
FIG. 9 is an enlarged assembled cross-sectional view of a portion of the frame and one of the constraints shown in FIG. 8, taken along line 8—8 of FIG. 7.

As shown best by FIGS. 6 and 9, the adjustment member 90 includes a grip 96, a threaded intermediate portion 98, and an extension 100. The grip 96 is suitably configured to be gripped for adjustment of the closing force. The closing force is discussed further below. The threaded intermediate portion 98 has suitable screw threads and is screwed into the reduced portion 71 of the opening 70. The base member 94 defines a slot 102 opening axially inward and an aperture 104 within the slot 102. Further, the base member 94 includes opposing ends 106 that fit into the enlarged portion 73 of the opening 70 to slidably engage the portion 64 of the frame 32. The extension 100 of the adjustment member 90 protrudes from the threaded intermediate portion 98 and slidably engages the base member 94 within the aperture 104.

The resilient member 92 is a coiled spring that is interposed between the threaded intermediate portion 98 of the adjustment member 90 and the base member 94. Using the resilient member 92, the force generator 88 generates a closing force that force closes the constraint system 34 about the patient's head. The closing force loads all the joints and ensures contact between the links and the joints. It should be readily appreciated that the force generator 88 generates the closing force generally coaxially with directional arrows 111. To this end, screwing the adjustment member 90 into the frame 32 generally increases the compression of the resilient member 92 as the head constraint member 86 presses against the head, thereby increasing the closing force of the constraint system 34—and vice versa. Because the resilient member 92 pushes in generally opposing directions against the end of the threaded intermediate portion 98 of the adjustment member 90 and against the base member 94, respectively, the closing force is generated generally coaxially with directional arrows 111. However, because the adjustment member 90 is screwed into the third portion 64 of the frame 32 and the first portion 60, the second portion 62, and the third portion 64 are all parts of the same frame 32, the frame 32 works to distribute the closing force so that all of the constraints are simultaneously loaded, which facilitates operation of the present invention.

The head constraint member 86 includes an elongated portion 108 that is slidably engaged with the slot 102 (generally parallel to the directional arrows 109) transversely to the closing force. Accordingly, it should be readily appreciated that this slidable engagement permits suitable freedom of the head constraint member 86 within the slot 102 along an axis generally parallel to the directional arrows 109. Further, it should be readily appreciated that movement of the base member 94 in the portion 64 of the frame 32 permits freedom of movement the base member 94 and the head constraint member 86 generally coaxially with—and subject to—the closing force provided by the resilient member 92 (see the directional arrows 111).

The elongated portion 108 includes bearings 110 at opposing ends that facilitate its slidable engagement with the slot 102. The bearings 110 shown are protruding portions of the elongated portion 108 that act as friction bearings. In alternative embodiments, the bearings 110 may be roller bearings, ball bearings, or any other suitable type of bearing. Moreover, it should be readily appreciated that alternative embodiments may suitably omit the distinct bearings 110. The head constraint member 86 further includes a generally pointed head 112 that is configured to pierce the skin of the patient's head and embed in the patient's skull during operation of the exemplary halo orthosis 30 of FIG. 4.

Applying the Grubler/Kutzbach criteria to determine the category of constraint provided by the frame 32 and the constraint system 34, the patient's head is modeled as one link and the frame 32 is modeled as one link, so that n=2. Further, the constraint 50 as a whole is modeled as one joint, the constraint 52 as a whole is modeled as one joint, and the constraint 54 as a whole is modeled as one joint, so that j=3. For the constraint 50, $f_1=3$ because taken individually the constraint 50 as a whole removes three degrees of linear freedom from the patient's head but permits three rotational degrees of freedom. However, for the constraint 52, $f_2=4$ because taken individually the constraint 52 as a whole removes two degrees of linear freedom from the skull but permits three rotational degrees of freedom, and further permits one degree of linear freedom generally parallel to directional lines 69. For the constraint 54, $f_3=5$ because taken individually the constraint 54 as a whole removes one degree of linear freedom from the skull but permits three rotational degrees of freedom, and further permits two degrees of linear freedom (one generally parallel to directional lines 109 and one generally coaxial to directional lines 111). The motion parameter is six because this is a spatial system, so that λ=6. Accordingly, applying the Grubler/Kutzbach criteria produces:

$$F = \lambda(n - j - 1) + \sum_{i=1}^{j} f_i$$

$F=6(2-3-1)+5+4+3$ $F=-12+12$ $F=0$

Thus, using the constraint system 34 shown in FIGS. 4–9, the head of a patient is exactly-constrained relative to the frame 32.

Figure 10:
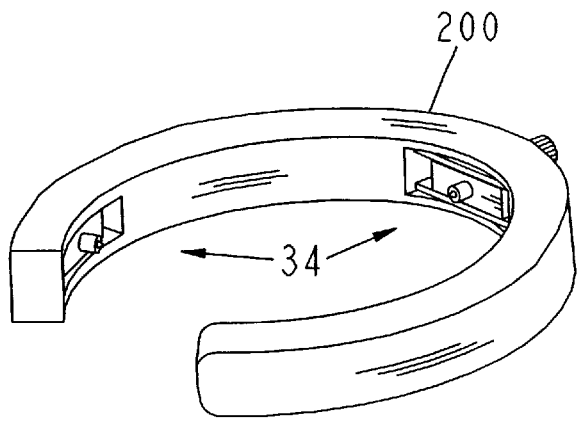
FIG. 10 is a perspective view of an alternative generally C-shaped frame with the constraint system shown in FIGS. 5–9.
Figure 11:
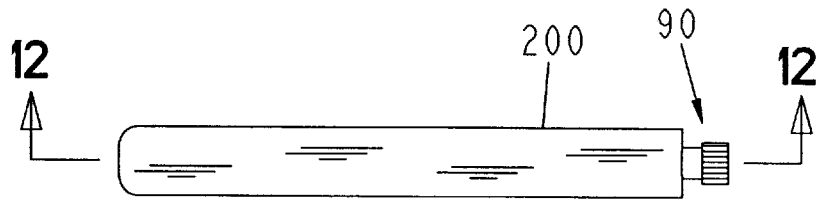
FIG. 11 is a side view of the alternative generally C-shaped frame and the constraint system shown in FIG. 10.
Figure 12:
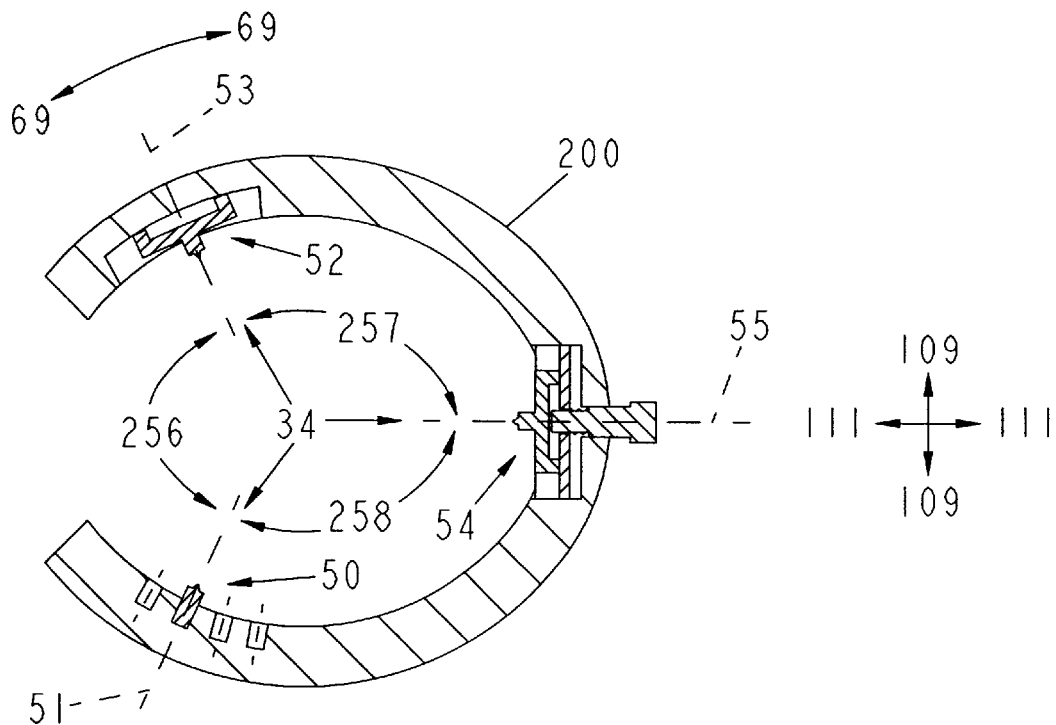
FIG. 12 is a cross-sectional view of the alternative generally C-shaped frame and the constraint system of FIG. 10 taken along line 12—12 of FIG. 11.

Another embodiment of the invention is shown in FIGS. 10–12. FIG. 10 shows a perspective view of an alternative generally C-shaped frame 200 combined with the constraint system 34 of FIGS. 4–9. A side view of the generally C-shaped frame 200 and the adjustment member 90 in shown in FIG. 11. FIG. 12 shows a cross-sectional view of the generally C-shaped frame 200 and the constraint system 34 of FIG. 10 along line 12—12 of FIG. 11. In general, the generally C-shaped frame 200 and the constraint system 34 are configured to engage the patient's head and to exactly constrain the head relative to the generally C-shaped frame 200 in the manner discussed above relative to FIGS. 4–9. Accordingly, the generally C-shaped frame 200 is also suitably made from MRI transparent materials such as an aluminum alloy, titanium and/or plastic(s), or any other suitable materials. It should be readily appreciated that the generally C-shaped frame 200 allows access to more of the back of the head than the oval-shaped frame 32 discussed above.

As discussed above relative to FIGS. 4–9, the constraint system 34 includes the constraint 50 which has an axis 51, the constraint 52 which has an axis 53, and the constraint 54 which has an axis 55. In the embodiment shown in FIGS. 10–12, the axis 51 is angularly displaced from the axis 53 by an angle 256, the axis 53 is angularly displaced from the axis 55 by angle 257, and the axis 55 is angularly displaced from the axis 51 by an angle 258. The constraint 50, the constraint 52, and the constraint 54 may be alternatively positioned about the generally C-shaped frame 200 according to a number of suitable alternative embodiments, as long as the angle 257 (between the constraint 52, which permits four degrees of relative motion, and the constraint 54, which permits five degrees of relative motion, discussed above) is not a multiple of 90 degrees (i.e., not 90 degrees, not 180 degrees, not 270 degrees, etc.). Further, as shown in FIG. 12, the angle 256, the angle 257, and the angle 258 preferably are each 120 degrees. However, these angles need not be equal in alternative embodiments.

Figure 13:
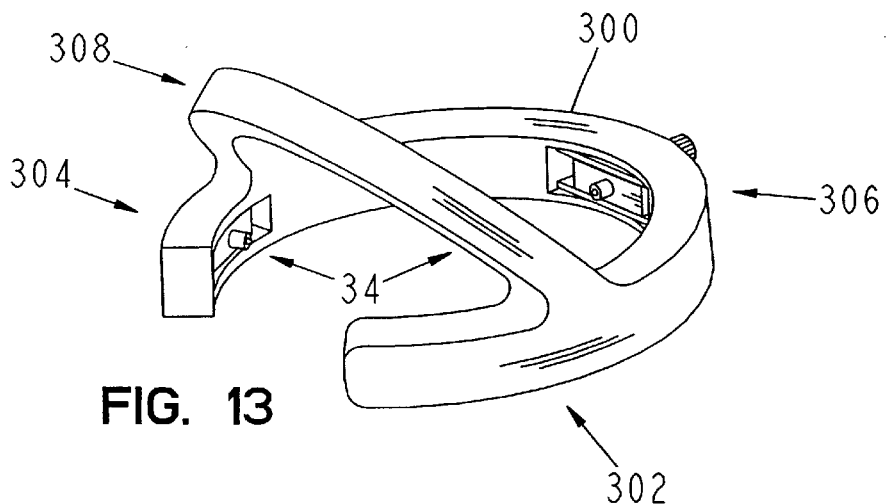
FIG. 13 is a perspective view of an alternative bridged generally C-shaped frame with the constraint system shown in FIGS. 5–9.
Figure 14:
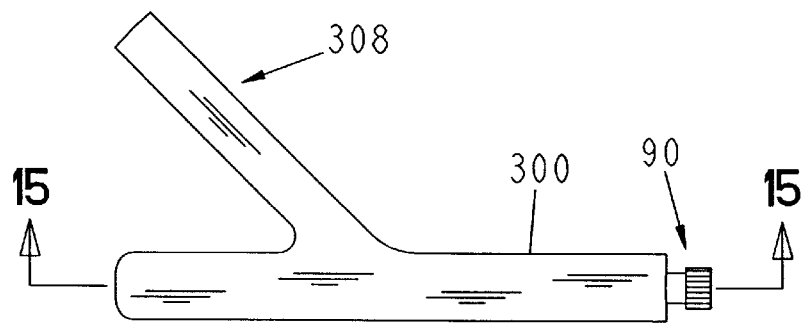
FIG. 14 is a side view of the alternative bridged generally C-shaped frame and the constraint system shown in FIG. 13.
Figure 15:
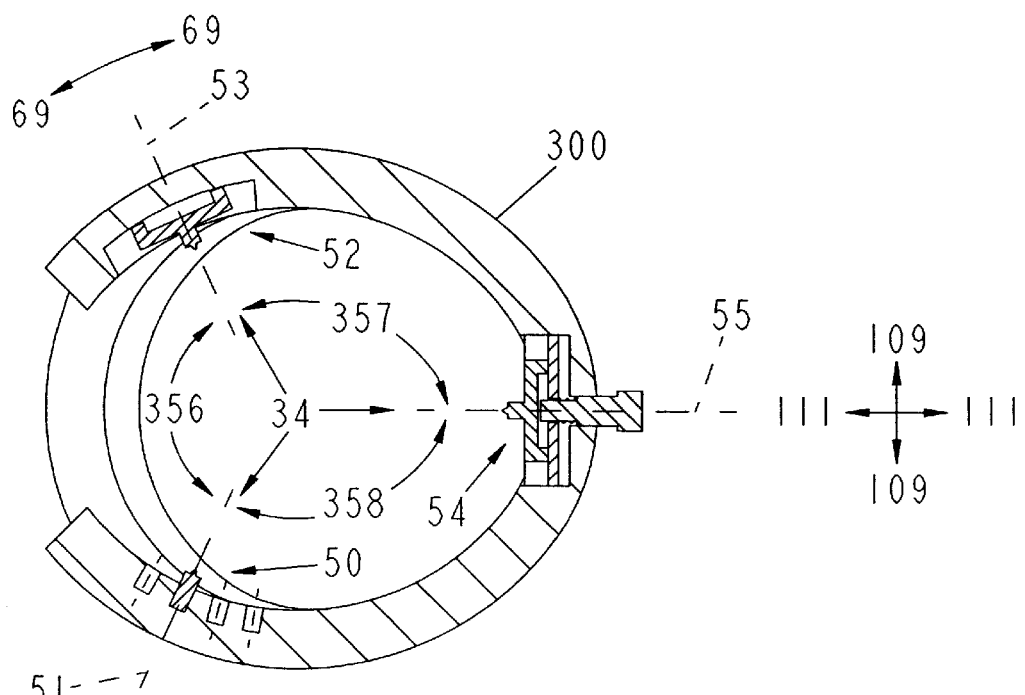
FIG. 15 is a cross-sectional view of the alternative bridged generally C-shaped frame and the constraint system of FIG. 13 taken along line 15—15 of FIG. 14.

Another embodiment of the invention is shown in FIGS. 13–15. FIG. 13 shows a perspective view of an alternative bridged generally C-shaped frame 300 combined with constraint system 34 of FIGS. 4–9. A side view of the bridged generally C-shaped frame 300 and the adjustment member 90 in shown in FIG. 14. FIG. 15 shows a cross-sectional view of the bridged generally C-shaped frame 300 and the constraint system 34 of FIG. 13 along line 15—15 of FIG. 14. In general, the bridged generally C-shaped frame 300 and the constraint system 34 are configured to engage the patient's head and to exactly constrain the head relative to the bridged generally C-shaped frame 300 in the manner discussed above relative to FIGS. 4–9. Accordingly, the bridged generally C-shaped frame 300 is also suitably made from MRI transparent materials such as an aluminum alloy, titanium and/or plastic(s), or any other suitable materials. As most fully shown by FIG. 13, a portion 302 of the bridged generally C-shaped frame 300, a portion 304 of the bridged generally C-shaped frame 300, and a portion 306 of the bridged generally C-shaped frame 300 are generally coplanar, and the bridged generally C-shaped frame 300 further includes a bridge 308 that defines a second plane which is angularly disposed from the general plane of the portion 302, the portion 304, and the portion 306. Generally, the bridge 308 strengthens the bridged generally C-shaped frame 300 and reduces susceptibility of the bridged generally C-shaped frame 300 to deformation in response to forces exerted on the constraint system 34 and the bridged generally C-shaped frame 300 by the patient's head. It should be readily appreciated that the bridged generally C-shaped frame 300 allows access to more of the back of the skull than the generally oval-shaped frame 32 discussed above, while also providing enhanced rigidity over the generally C-shaped frame 200 discussed above.

As discussed above relative to FIGS. 4–9, the constraint system 34 includes the constraint 50 which has an axis 51, the constraint 52 which has an axis 53, and the constraint 54 which has an axis 55. In the embodiment shown in FIGS. 13–15, the axis 51 is angularly displaced from the axis 53 by an angle 356, the axis 53 is angularly displaced from the axis 55 by angle 357, and the axis 55 is angularly displaced from the axis 51 by an angle 358. The constraint 50, the constraint 52, and the constraint 54 may be alternatively positioned about the bridged generally C-shaped frame 300 according to a number of suitable alternative embodiments, as long as the angle 357 (between the constraint 52, which permits four degrees of relative motion, and the constraint 54, which permits five degrees of relative motion, discussed above) is not a multiple of 90 degrees (i.e., not 90 degrees, not 180 degrees, not 270 degrees, etc.). Further, as shown in FIG. 15, the angle 356, the angle 357, and the angle 358 preferably are each 120 degrees. However, these angles need not be equal in alternative embodiments.

Figure 16:
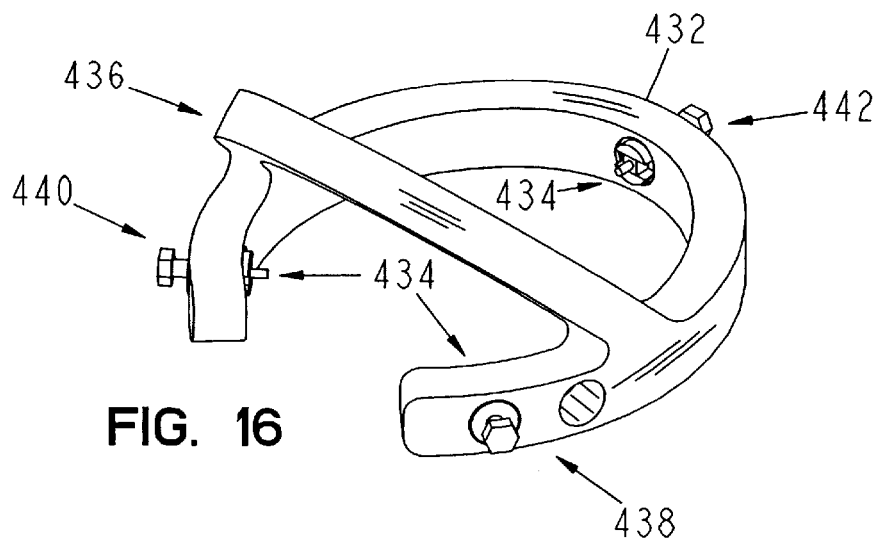
FIG. 16 is a perspective view of an alternative bridged generally C-shaped frame with an alternative constraint system constructed according to the present invention.
Figure 17:
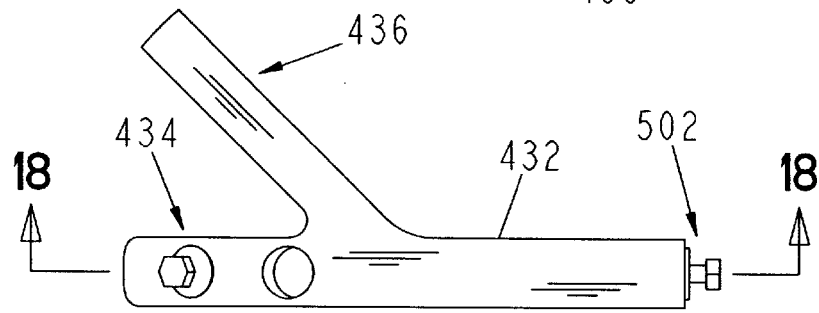
FIG. 17 is a side view of the bridged generally C-shaped frame and the constraint system of FIG. 16.

Another embodiment of the invention is shown in FIGS. 16–24. FIG. 16 shows a perspective view of an alternative bridged generally C-shaped frame 432 combined with an alternative embodiment of a constraint system 434 constructed according to the present invention. A side view of the bridged generally C-shaped frame 432 and the constraint system 434 is shown in FIG. 17. In general, the bridged generally C-shaped frame 432 and the constraint system 434 are configured to engage the patient's head and to exactly constrain the head relative to the bridged generally C-shaped frame 432. Accordingly, the bridged generally C-shaped frame 432 and the constraint system 434 are also suitably made from MRI transparent materials such as an aluminum alloy, titanium and/or plastic(s), or any other suitable materials.

As most fully shown by FIG. 16, the bridged generally C-shaped frame 432 includes a portion 438, a portion 440, and a portion 442 that are generally coplanar, and further includes a bridge 436 that defines a second plane which is angularly disposed from the general plane of the portion 438, the portion 440, and the portion 442. Generally, the bridge 436 strengthens the bridged generally C-shaped frame 432 and reduces susceptibility of the bridged generally C-shaped frame 432 to deformation in response to forces exerted on the constraint system 434 and the bridged generally C-shaped frame 432 by the patient's head. It should be readily appreciated that the bridged generally C-shaped frame 432 allows access to more of the back of the skull than the generally oval-shaped frame 32 discussed above, while also providing enhanced rigidity over the generally C-shaped frame 200 discussed above.

Figure 18:
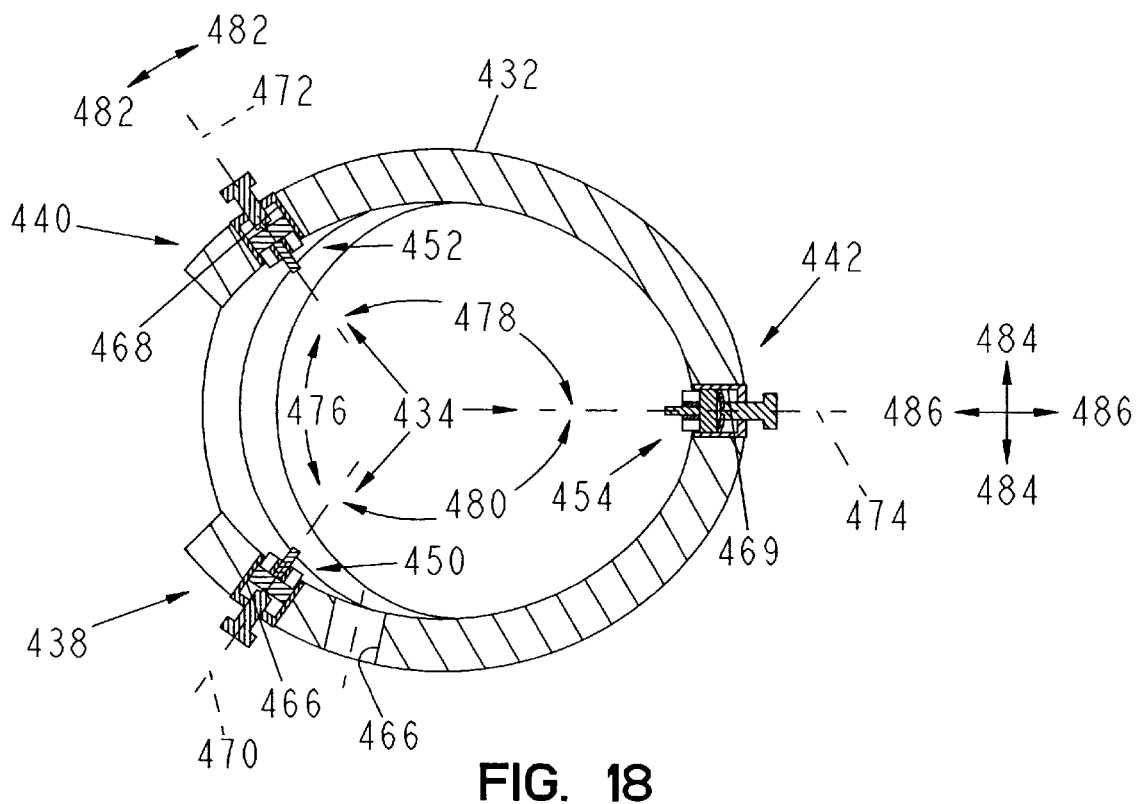
FIG. 18 is a cross-sectional view of the bridged generally C-shaped frame and the constraint system of FIG. 16 taken along line 18—18 of FIG. 17.

The constraint system 434 is shown in greater detail in the cross-section view of frame 432 (taken along line 18-18 of FIG. 17) shown in FIG. 18. As discussed above, the bridged generally C-shaped frame 432 includes the portion 438, the portion 440, and the portion 442. As shown FIG. 18, the constraint system 434 includes a constraint 450, a constraint 452, and a constraint 454. The portion 438 of the bridged generally C-shaped frame 432 defines a set of apertures 466. It should be readily appreciated that although two apertures are shown, the set of apertures 466 may suitably include a number of apertures other than two. In any event, each of the apertures 466 includes suitable screw threads (not shown) and is suitably sized to receive the constraint 450 as discussed in further detail below. Similarly, the portion 440 of the bridged generally C-shaped frame 432 defines an aperture 468 that includes suitable screw threads (not shown) and is suitably sized to receive the constraint 452, and the portion 442 of the bridged generally C-shaped frame 432 defines an aperture 469 that includes suitable screw threads (not shown) and is suitably sized to receive the constraint 454. It should be readily appreciated that the constraint 452 and constraint 454 are shown installed in the apertures 468 and 469, respectively, and the constraint 450 is shown installed in one of the apertures 466.

The constraint 450 has an axis 470, the constraint 452 has an axis 472, and the constraint 454 has an axis 474. The axis 470 is angularly displaced from the axis 472 by an angle 476, the axis 472 is angularly displaced from the axis 474 by angle 478, and the axis 474 is angularly displaced from the axis 470 by an angle 480. It should be readily appreciated that the apertures in the bridged generally C-shaped frame 432 (and thus the constraint 450, the constraint 452, and the constraint 454) may be alternatively positioned about the bridged generally C-shaped frame 432 according to a number of suitable alternative embodiments, as long as the angle 478 (between the constraint 452, which permits four degrees of relative motion, and the constraint 454, which permits five degrees of relative motion, discussed below) is not a multiple of 90 degrees (i.e., not 90 degrees, not 180 degrees, not 270 degrees, etc.). Further, as shown in FIG. 18, the angle 476, the angle 478, and the angle 480 preferably are each 120 degrees. However, these angles need not be equal in alternative embodiments. As discussed in further detail below, the constraint 452 permits suitable freedom movement of a head constraint member along an axis generally parallel to the directional arrows 482. Also, as discussed in further detail below, the constraint 454 permits suitable freedom of another head constraint member along an axis generally parallel to the directional arrows 484 and generally coaxially with a closing force (see the directional arrows 486).

Figure 19:
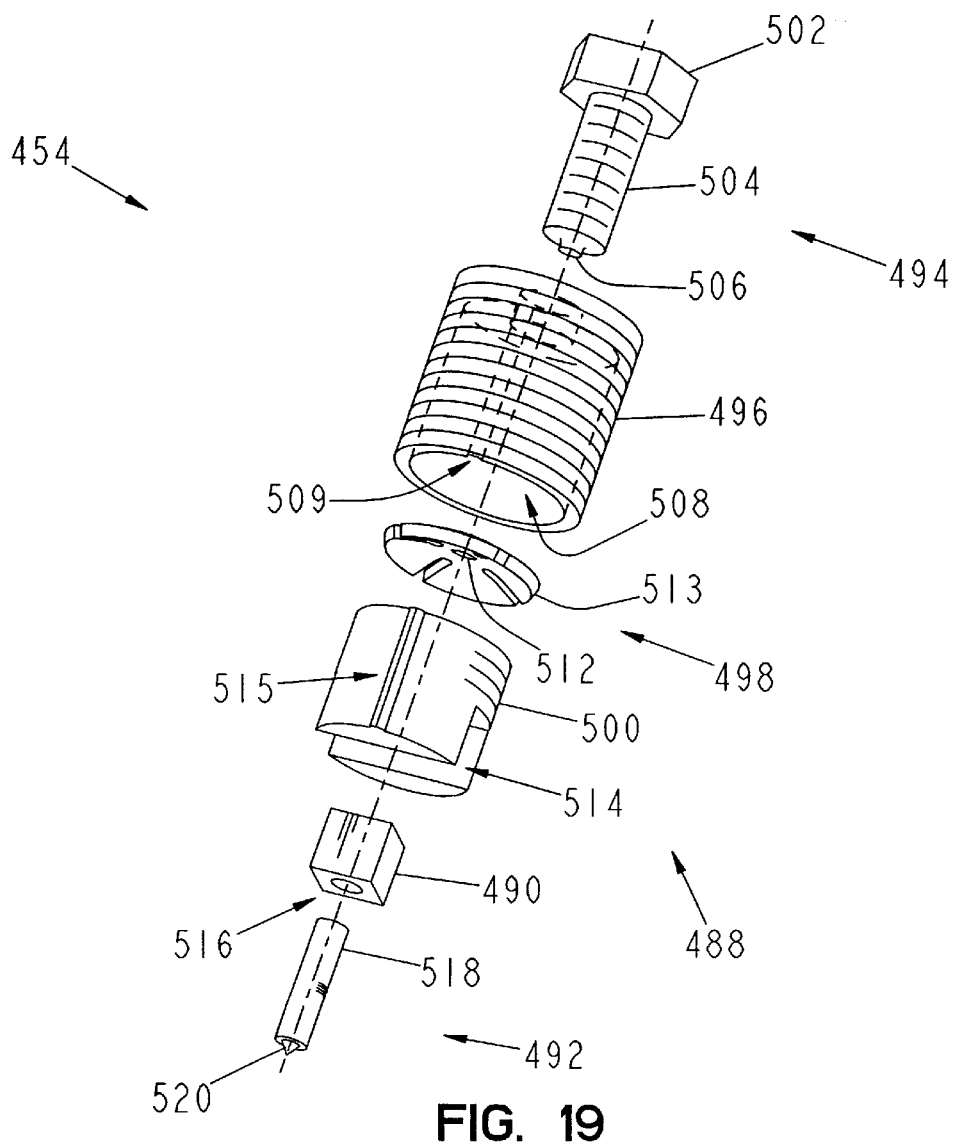
FIG. 19 is an exploded perspective view of a constraint of the constraint system of FIG. 18.
Figure 20:
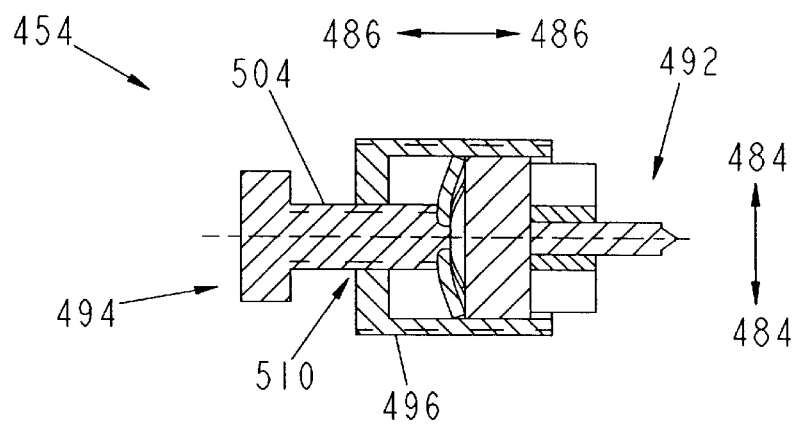
FIG. 20 is an enlarged assembled cross-sectional view of the constraint shown in FIG. 19 taken along line 18—18 of FIG. 17.

The constraint 454 of the constraint system 434 is shown in greater detail in FIGS. 19 and 20. FIG. 19 is an exploded perspective view of the constraint 454, and FIG. 20 is an enlarged assembled cross-sectional view of the constraint 454 taken along line 18—18 of FIG. 17 (see also FIG. 18). The constraint 454 includes a force generator 488, a bearing 490, and a head constraint member 492. The force generator 488 includes an adjustment member 494, a sleeve 496, a resilient member 498, and a base member 500. The adjustment member 494 includes a grip 502, a threaded intermediate portion 504, and an extension 506. The grip 502 is hexagonally-shaped or otherwise suitably configured to be gripped for adjustment of a closing force provided by the force generator 488. The closing force is discussed in further detail below. The threaded intermediate portion 504 has suitable screw threads. The extension 506 protrudes from the threaded intermediate portion 504.

The sleeve 496 defines a generally cylindrical cavity 508 and a longitudinal channel 509 in the perimeter of the cavity 508. The cavity 508 is suitably sized to receive the base member 500 and the resilient member 498 as discussed in further detail below. The sleeve 496 also defines an aperture 510 (see FIG. 20) that is suitably sized and screw threaded to receive the threaded intermediate portion 504 of the adjustment member 494. Further, the sleeve 496 has suitable screw threads on its exterior perimeter surface, by which the sleeve 496 screws into the aperture 469 in the portion 442 of the generally C-shaped frame 432 (see FIG. 18). Further, the sleeve 496 is fixed within the aperture 469 by soldering, gluing, or any other suitable manner.

The resilient member 498 is a generally dome-shaped spring that is suitably sized to fit within the generally cylindrical cavity 508 of the sleeve 496. Further, the resilient member 498 defines an aperture 512 that is suitably sized to receive the extension 506 of the adjustment member 494.

The base member 500 has a longitudinal ridge 515 that is sized to be slidably received in the longitudinal channel 509 of the cavity 508 defined by the sleeve 496. Further, the base member 500 defines a slot 514 that is sized to receive the bearing 490. The bearing 490 is a generally cubed-shaped member that is suitably sized to slidably engage the slot 514. Further, the bearing 490 defines an aperture 516. The aperture 516 is suitably sized to receive the head constraint member 492 as discussed in further detail below.

The head constraint member 492 includes a member 518 that is generally cylindrical and sized to fit into the aperture 516 of the bearing 490. The head constraint member 492 further includes a generally pointed head 520 that protrudes from the member 518. The generally pointed head 520 is configured to pierce the skin of a patient's head and embed in the patient's skull during operation.

When assembled, the threaded intermediate portion 504 of the adjustment member 494 is screwed through the aperture 510 and the resilient member 498 is housed within the cavity 508 of the sleeve 496. Further, the extension 506 protrudes into the aperture 512 of the resilient member 498, and the rim 513 of the resilient member 498 engages the base member 500. The base member 500 is slidably received within the cavity 508 defined by the sleeve 496, and the longitudinal ridge 515 of the base member 500 is slidably received within the longitudinal channel 509 of the cavity 508. Further, the bearing 490 slidably fits within the slot 514. The member 518 is fixed in the aperture 516 of the bearing 490 by a compression fit, soldering, gluing, or any other suitable manner. Accordingly, it should be readily appreciated that in alternative embodiments, the head constraint member 492 (which includes the member 518) and the bearing 490 may suitably be integrated into a single part.

It should be readily appreciated that the force generator 488 generates the closing force that force closes the constraint system 434 similarly to the manner in which the force generator 88 generates the closing force in the alternative embodiments discussed above. In the embodiment shown in FIGS. 16–24, the force generator 488 generates the closing force generally coaxially with directional arrows 486 (see also FIG. 18). Screwing the adjustment member 494 into the sleeve 496 generally increases the compression of the resilient member 498 as the head constraint member 492 presses against the skull, thereby increasing the closing force of the constraint system 434 (see FIG. 18)—and vice versa Because the resilient member 498 pushes in generally opposing directions against the end of the threaded intermediate portion 504 of the adjustment member 494 and against the base member 500, respectively, the closing force is generated generally along directional arrows 486. Further, because the adjustment member 494 is screwed into the sleeve 496, which is screwed into the portion 442 of the generally C-shaped frame 432 (see FIG. 18) and the portion 438, the portion 440, and the portion 442 are all parts of the same generally C-shaped frame 432, the generally C-shaped frame 432 works to distribute the closing force and simultaneously load the constraints, which facilitates operation of the present invention. Further, it should be readily appreciated that in the embodiment shown in FIGS. 16–24, the slidable relationship between the base member 500 and the sleeve 496 permits suitable freedom of the base member 500 and the head constraint member 492 generally coaxially with—and subject to—the closing force provided by the resilient member 498 (see the directional arrows 486). The engagement between the longitudinal ridge 515 of the base member 500 and the longitudinal channel 509 defined by the sleeve 496 prevents the base member 500 (and thus the slot 514) from rotating in the sleeve 496. Additionally, the slidable relationship between the bearing 490 and the slot 514 (see FIG. 19) permits movement of the head constraint member 492 within the slot 514 along an axis generally parallel to the directional arrows 484 (see FIGS. 18 and 20).

Figure 21:
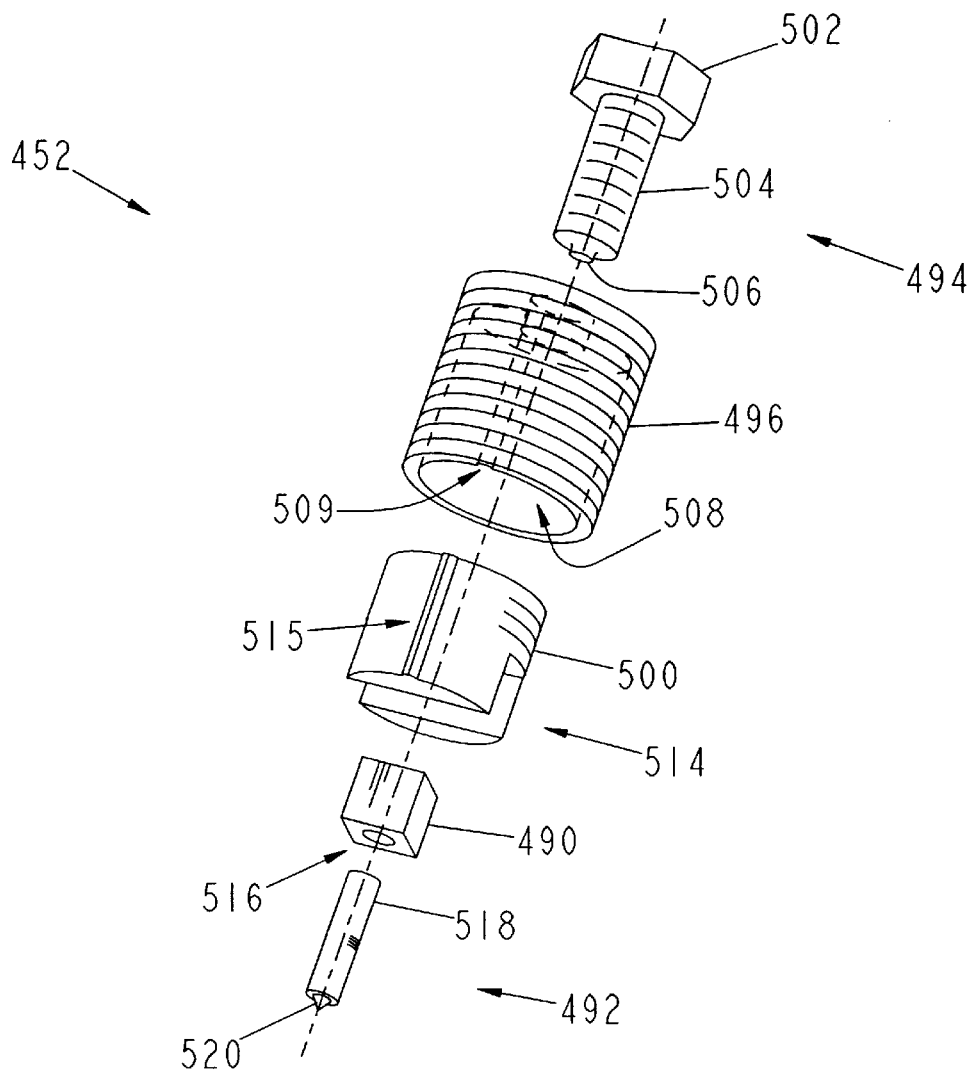
FIG. 21 is an exploded perspective view of another constraint of the constraint system shown in FIG. 18.
Figure 22:
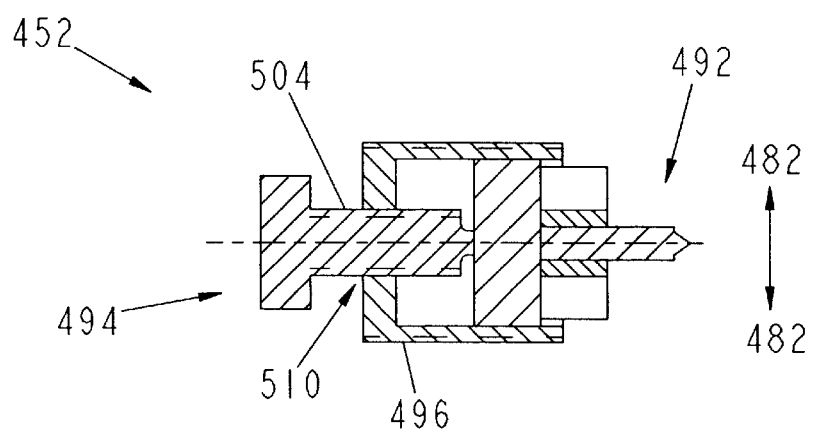
FIG. 22 is an enlarged assembled cross-sectional view of the constraint shown in FIG. 21 taken along line 18—18 of FIG. 17.

The constraint 452 of the constraint system 434 is shown in further detail in FIGS. 21 and 22. FIG. 21 is an exploded perspective view of the constraint 452, and FIG. 22 is an enlarged assembled cross-sectional view of the constraint 452 taken along line 18—18 of FIG. 17 (see also FIG. 18). It should be readily appreciated that the constraint 452 is made from like parts as the constraint 454, discussed above, except for the removal of the resilient member 498 (see FIG. 18). Further, it should be readily appreciated that without the resilient member 498, extension 506 of the adjustment member 494 abuts the base member 500 (see FIG. 22) which effectively negates the slidable relationship between the base member 500 and the sleeve 496, while the slidable relationship between the bearing 490 and the slot 514 still permits movement of the head constraint member 492 within the slot 514 along an axis generally parallel to the directional arrows 484 of FIG. 21.

Figure 23:
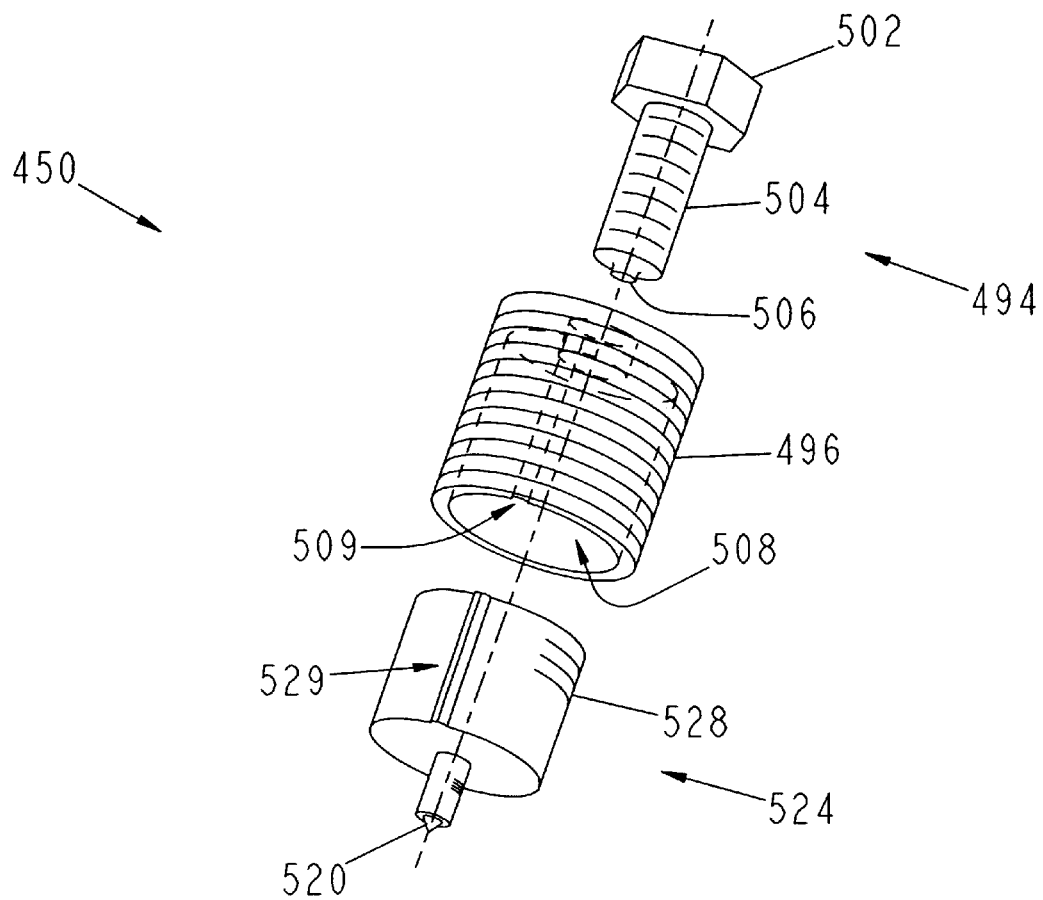
FIG. 23 is an exploded perspective view of another constraint of the constraint system shown in FIG. 18.
Figure 24:
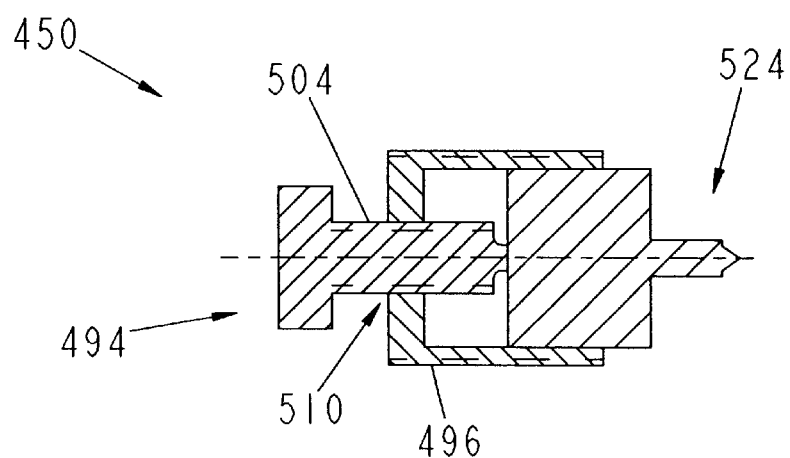
FIG. 24 is an enlarged assembled cross-sectional view of the constraint shown in FIG. 23 along line 18—18 of FIG. 17.

The constraint 450 of the constraint system 434 is shown in further detail in FIGS. 23 and 24. FIG. 23 is an exploded perspective view of the constraint 450, and FIG. 24 is an enlarged assembled cross-sectional view of the constraint 450 taken along line 18—18 of FIG. 17 (see also FIG. 18). It should be readily appreciated that the constraint 450 is made from like parts as the constraint 452, discussed above, except for the replacement of the base member 500, the bearing 490, and the member 518 (see FIG. 21) with one solid head constraint member 524. Accordingly, the head constraint member 524 includes a base member 528 in combination with the generally pointed head 520. The base member 528 is sized to be slidably received within the cavity 508 defined by the sleeve 496. Further, the base member 528 has a longitudinal ridge 529 that is sized to be slidably received within the longitudinal channel 509 of the cavity 508. The engagement between the longitudinal ridge 529 of the base member 528 and the longitudinal channel 509 defined by the sleeve 496 prevents the base member 528 from rotating in the sleeve 496. It should be readily appreciated that with the removal of the slidable relationship between the bearing 490 and the slot 514 (see FIG. 21) the head constraint member 524 is effectively fixed within the sleeve 496 of the constraint 450.

Applying the Grubler/Kutzbach criteria to determine the category of constraint provided by the bridged generally C-shaped frame 432 combined with the constraint system 434, the patient's head is modeled as one link and the bridged generally C-shaped frame 432 is modeled as one link, so that n=2. Further, the constraint 450 as a whole is modeled as one joint, the constraint 452 as a whole is modeled as one joint, and the constraint 454 as a whole is modeled as one joint, so that j=3. For the constraint 450, $f_1=3$ because taken individually the constraint 450 as a whole removes three degrees of linear freedom from the patient's head but permits three rotational degrees of freedom. However, for the constraint 452, $f_2=4$ because taken individually the constraint 452 as a whole removes two degrees of linear freedom from the skull but permits three rotational degrees of freedom, and further permits one degree of linear freedom generally parallel to directional lines 482. For the constraint 454, $f_3=5$ because taken individually the constraint 454 as a whole removes one degree of linear freedom from the skull but permits three rotational degrees of freedom, and further permits two degrees of linear freedom (one generally parallel to directional lines 484 and one generally coaxial to directional lines 486). The motion parameter is six because this is a spatial system, so that $\lambda=6$. Accordingly, applying the Grubler/Kutzbach criteria produces:

$$F = \lambda(n - j - 1) + \sum_{i=1}^{j} f_i$$

$F=6(2-3-1)+5+4+3$ $F=-12+12$ $F=0$

Thus, using the constraint system 434 shown in FIGS. 16–24, the head of a patient is exactly-constrained relative to the bridged generally C-shaped frame 432.

Figure 25:
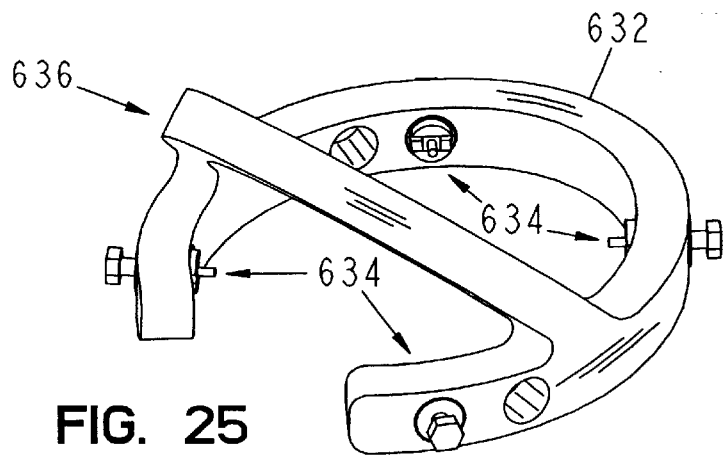
FIG. 25 is a perspective view of an alternative bridged generally C-shaped frame with an alternative constraint system constructed according to the present invention.
Figure 26:
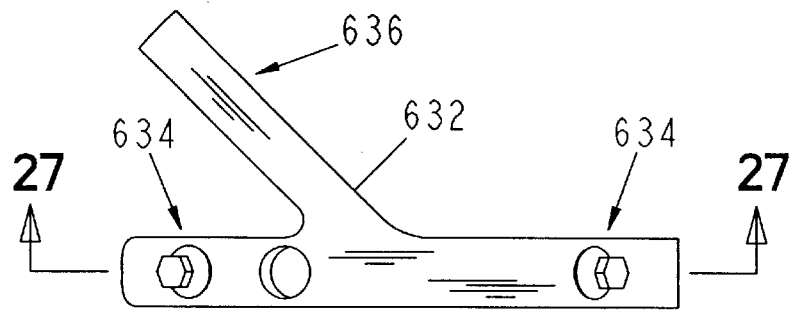
FIG. 26 is a side view of the bridged generally C-shaped frame and the constraint system shown in FIG. 25.
Figure 27:
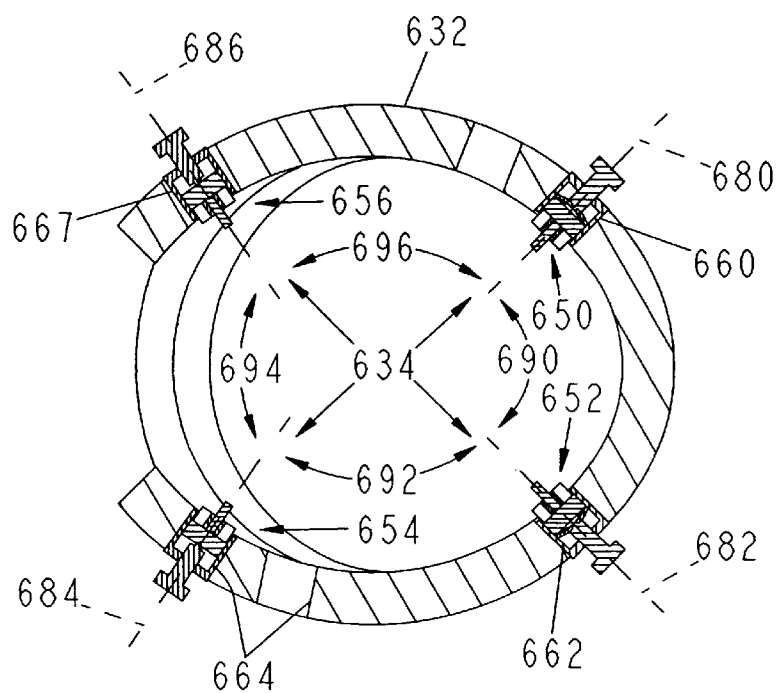
FIG. 27 is a cross-sectional view of the bridged generally C-shaped frame and the constraint system of FIG. 25 taken along line 27—27 of FIG. 26.

As shown in FIGS. 25–27, another embodiment of the invention includes an alternative bridged generally C-shaped frame 632 with an alternative constraint system 634 constructed according to the present invention. It should be readily appreciated that the bridged generally C-shaped frame 632 is similarly to the bridged generally C-shaped frame 432 discussed above (see FIGS. 16–18), except the bridged generally C-shaped frame 632 accommodates four constraints (a constraint 650, a constraint 652, a constraint 654, and a constraint 656) as shown best in FIG. 27. The bridged generally C-shaped frame 632 receives the constraint 650 in a threaded aperture 660, receives the constraint 654 in a threaded aperture 662, receives the constraint 654 in one of a set of threaded apertures 664 (which, although shown as two apertures, may be a number of apertures other than two), and receives the constraint 656 in a threaded aperture 667. Constraint 650 and constraint 652 are each configured in the same manner as constraint 454 (discussed above relative to FIGS. 19 and 20), while constraint 654 and constraint 656 are each configured in the same manner as constraint 452 (discussed above relative to FIGS. 20 and 21).

In the embodiment shown in FIGS. 25–27, the constraint 650 has an axis 680, the constraint 652 has an axis 682, the constraint 654 has an axis 684, and the constraint 656 has an axis 686. The axis 680 is angularly displaced from the axis 682 by an angle 690, the axis 682 is angularly displaced from the axis 684 by angle 692, the axis 684 is angularly displaced from the axis 686 by an angle 694, and the axis 686 is angularly displaced from the axis 680 by an angle 696. The constraint 650, the constraint 652, the constraint 654, and the constraint 656 may be alternatively positioned about the bridged generally C-shaped frame 632 according to a number of suitable alternative embodiments, as long as neither the angle 696 (between the constraint 650, which permits five degrees of relative motion, and the constraint 656, which permits four degrees of relative motion, discussed below) nor the angle 692 (between the constraint 652, which permits five degrees of relative motion, and the constraint 654, which permits four degrees of relative motion, discussed below) is 180 degrees, and as long as not all of the slots 514 (see FIGS. 19 and 21) of the constraints are coplanar (discussed further below in connection with operation of the invention). As shown in FIG. 27, the angle 690, the angle 692, the angle 694, and the angle 696 preferably are each about 90 degrees. However, these angles need not be equal in alternative embodiments.

Applying the Grubler/Kutzbach criteria to determine the category of constraint provided by the bridged generally C-shaped frame 632 combined with the constraint system 634, the patient's head is modeled as one link and the bridged generally C-shaped frame 632 is modeled as one link, so that n=2. Further, the constraint 650 as a whole is modeled as one joint, the constraint 652 as a whole is modeled as one joint, the constraint 654 as a whole is modeled as one joint, and the constraint 656 as a whole is modeled as one joint, so that j=4. For the constraint 650, $f_1=5$ because taken individually the constraint 650 as a whole removes one degree of linear freedom from the skull but permits three rotational degrees of freedom, and further permits two degrees of linear freedom. Likewise, for the constraint 652, $f_2=5$ because taken individually the constraint 652 as a whole removes one degree of linear freedom from the skull but permits three rotational degrees of freedom, and further permits two degrees of linear freedom. For the constraint 654, $f_3=4$ because taken individually the constraint 654 as a whole removes two degrees of linear freedom from the skull but permits three rotational degrees of freedom, and further permits one degree of linear freedom. Likewise, for the constraint 656, $f_4=4$ because taken individually the constraint 656 as a whole removes two degrees of linear freedom from the skull but permits three rotational degrees of freedom, and further permits one degree of linear freedom. The motion parameter is six because this is a spatial system, so that $\lambda=6$. Accordingly, applying the Grubler/Kutzbach criteria produces:

$$F = \lambda(n - j - 1) + \sum_{i=1}^{j} f_i$$

$F=6(2-4-1)+5+5+4+4$ $F=-18+18$ $F=0$

Thus, using the constraint system 634 shown in FIGS. 25–27, the head of a patient is exactly-constrained relative to the bridged generally C-shaped frame 632.

Operation of the various embodiments of the invention can best be described by referring to the exemplary halo orthosis 30 of FIG. 4. The frame 32 and the resilient member 92 are suitably tailor made to fit the size of the particular patient's head (or suitably selected from a range of various stock pieces) such that, in general, after suitable adjustment of the adjustment member 90 of the force generator 88 all of the head constraint members are firmly but safely embedded in the skull, yet the head constraint member 74 is still sufficiently free to move generally parallel to directional arrows 69 and the head constraint member 86 (in combination with the base member 94) is still sufficiently free to move generally parallel to directional arrows 109 and generally coaxially with directional arrows 111 so as to accommodate typical physiological changes in the skull that may occur from time to time.

Further, the support structure 36 is suitably fitted onto the patient and suitably aligned in any of various manners which are well known. Next, the head constraint member 72 is screwed into the most suitable one of the apertures 66 of the frame 32 and fixed in that aperture by soldering, gluing, or any other suitable manner. The frame 32 is placed around the patient's head such that the axes of the constraint 50, the constraint 52, and the constraint 54 are suitably aligned with the desired sites of the patient's skull. It should be readily appreciated that the adjustment member 90 of the force generator 88 may be adjusted or removed as necessary to facilitate the alignment. After the constraints are aligned with the desired sites, the closing force from the force generator 88 is adjusted to the desired amount by suitably screwing the adjustment member 90 of the force generator 88 into and/or out of the frame 32. A torque wrench may used in the manipulation of the adjustment member 90 in order to set the closing force to an accurate desired level. Similar operation of alternative embodiments of the present invention should be readily appreciated.

However, it is noted that in operation of the embodiment shown in FIGS. 25–27, the slot 514 of the constraint 650, the slot 514 of the constraint 652, the slot 514 of the constraint 654, and the slot 514 of the constraint 656 (see FIGS. 19 and 21) are not all aligned in the same plane; i.e., the directional lines 484 of at least one of the constraints (see FIGS. 20 and 22) must lie in a different plane than the directional lines 484 of the other constraints. This skewing of one or more of the slots is effectuated by suitably slightly rotating (screwing in or out) one or more of sleeve 496 of the constraint 650, sleeve 496 of the constraint 652, sleeve 496 of the constraint 654, and sleeve 496 of the constraint 656 (see FIGS. 19 and 21) within the aperture 660, the aperture 662, one of the apertures 664, and the aperture 667 of the bridged generally C-shaped frame 632, respectively, and then fixing each sleeve 496 within the respective aperture by soldering, gluing, or any other suitable manner.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

What is claimed is:

1. An apparatus for restricting movement of a patient's head, the apparatus comprising:
   a frame; and
   a plurality of constraints engaged with the frame to exactly constrain the patient's head relative to the frame, wherein the plurality of constraints includes a first constraint engaged with the frame to permit exactly three degrees of motion of the patient's head relative to the frame, a second constraint engaged with the frame to permit exactly four degrees of motion of the patient's head relative to the frame, and a third constraint engaged with the frame to permit exactly five degrees of motion of the patient's head relative to the frame.

2. The apparatus of claim 1, wherein the first constraint is engaged with the frame to permit three degrees of rotational motion of the patient's head relative to the frame, the second constraint is engaged with the frame to permit three degrees of rotational motion of the patient's head relative to the frame and one degree of linear motion of the patient's head relative to the frame, and the third constraint is engaged with the frame to permit three degrees of rotational motion of the patient's head relative to the frame and two degrees of linear motion of the patient's head relative to the frame.

3. An apparatus for restricting movement of a patient's head, the apparatus comprising:
   a frame; and
   a plurality of constraints engaged with the frame to exactly constrain the patient's head relative to the frame, wherein the plurality of constraints includes a constraint engaged with the frame to permit exactly five degrees of motion of the patient's head relative to the frame, wherein the constraint includes:
   a first member engaged with a portion of the frame to move generally along an axis; and
   a second member configured to pierce the patient's head and embed in the patient's skull, the second member engaged with the first member to move transversely to the axis.

4. The apparatus of claim 3, wherein:
the first member of the constraint defines a slot; and
the second member of the constraint is movably engaged with the first member within the slot.

5. The apparatus of claim 4, wherein:
the portion of the frame defines an opening;
the constraint further includes a fourth member within the opening defined by the portion of the frame; and
the constraint further includes a resilient member interposed between the fourth member and the first member.

6. The apparatus of claim 5, wherein the resilient member includes a coiled spring.

7. An apparatus for restricting movement of a patient's head, the apparatus comprising:
   a frame; and
   a plurality of constraints engaged with the frame to exactly constrain the patient's head relative to the frame, wherein the plurality of constraints includes a constraint engaged with the frame to permit exactly five degrees of motion of the patient's head relative to the frame, wherein the constraint includes:
   a sleeve engaged with a portion of the frame;
   a first member engaged with the sleeve to move generally along an axis; and
   a second member engaged with the first member to move transversely to the axis.

8. The apparatus of claim 7, wherein:
the sleeve defines a cavity;
the first member of the constraint is received within the cavity and defines a slot; and
the second member of the constraint is movably engaged with the first member within the slot.

9. The apparatus of claim 8, wherein:
the second member of the constraint defines a first aperture;
the constraint further includes a third member positioned within the first aperture; and
the third member is configured to pierce the head of the patient and embed in the skull.

10. The apparatus of claim 9, wherein:
the sleeve further defines a second aperture;
the constraint further includes a third member within the second aperture; and
the constraint further includes a resilient member interposed between the third member and the first member.

11. The apparatus of claim 10, wherein the resilient member includes a generally dome-shaped spring.

12. An apparatus for restricting movement of a patient's head, the apparatus comprising:

a frame; and a plurality of constraints engaged with the frame to exactly constrain the patient's head relative to the frame, wherein the plurality of constraints includes a constraint engaged with the frame to permit exactly four degrees of motion of the patient's head relative to the frame, wherein the constraint includes: a sleeve engaged with a portion of the frame, the sleeve defining a cavity; a first member defining a slot that is received within the cavity; and a second member that is movably engaged with the first member within the slot, wherein the second member of the constraint defines a first aperture; the constraint further includes a third member positioned within the first aperture; and the third member is configured to pierce the head of the patient and embed in the skull, and wherein the sleeve further defines a second aperture; the constraint further includes a third member within the second aperture; and the third member abuts the first member.

\* \* \* \* \*